(12) United States Patent
Maertens et al.

(10) Patent No.: US 6,855,318 B1
(45) Date of Patent: Feb. 15, 2005

(54) MULTI-MER PEPTIDES DERIVED FROM HEPATITIS C VIRUS ENVELOPE PROTEINS FOR DIAGNOSTIC USE AND VACCINATION PURPOSES

(75) Inventors: Geert Maertens, Brugge (BE); Erik Depla, Dealalbergen (BE)

(73) Assignee: N.V. Innogenetics S.A., Ghent (BE)

( * ) Notice: Subject to any disclaimer, the term of this patent is extended or adjusted under 35 U.S.C. 154(b) by 0 days.

(21) Appl. No.: 09/566,266

(22) Filed: May 5, 2000

Related U.S. Application Data

(63) Continuation of application No. PCT/EP98/07105, filed on Nov. 6, 1998.

(30) Foreign Application Priority Data

Nov. 6, 1997 (EP) ............................................. 97870179

(51) Int. Cl.⁷ ......................... A61K 39/00; A61K 39/29; G01N 33/53; G01N 33/536; C12N 15/09
(52) U.S. Cl. ................................. 424/189.1; 424/228.1; 514/2; 435/5; 435/7.1; 435/7.92; 435/69.1; 435/69.3
(58) Field of Search ........................... 435/5, 7.1, 69.1, 435/69.3; 530/317, 321, 324, 300, 325, 326; 424/185.1, 186.1, 189.1, 204.1, 228.1; 514/2; 436/518

(56) References Cited

U.S. PATENT DOCUMENTS

| | | | |
|---|---|---|---|
| 5,670,153 A | * | 9/1997 | Weiner et al. ............ 424/189.1 |
| 5,747,239 A | | 5/1998 | Wang et al. |

FOREIGN PATENT DOCUMENTS

| | | |
|---|---|---|
| EP | 0 445 423 | 9/1991 |
| EP | 0 468 527 | 1/1992 |
| WO | WO 93 02103 | 2/1993 |
| WO | WO 93 06247 | 4/1993 |
| WO | WO 93 06488 | 4/1993 |
| WO | WO93/18054 | 9/1993 |
| WO | WO 94 25874 | 11/1994 |
| WO | WO 95 12677 | 5/1995 |
| WO | WO 95 32291 | 11/1995 |
| WO | WO 96 04385 | 2/1996 |

* cited by examiner

*Primary Examiner*—James Housel
*Assistant Examiner*—Zachariah Lucas
(74) *Attorney, Agent, or Firm*—Nixon & Vanderhye P.C.

(57) ABSTRACT

Multimer peptides (e.g. 30- to 45-mer peptides) derived from hepatitis C virus envelope proteins reacting with the majority of anti-HCV antibodies present in patient sera are described. The usage of the latter peptides to diagnose, and to vaccinate against, an infection with hepatitis C virus is also disclosed.

29 Claims, 4 Drawing Sheets

Figure 1:
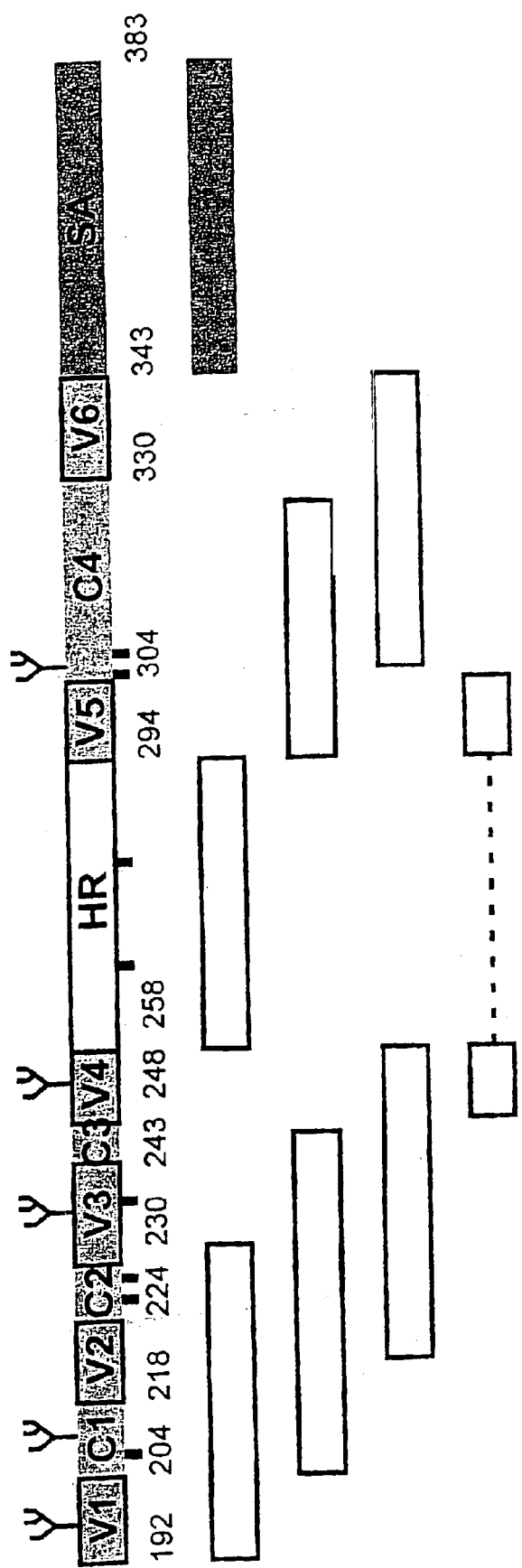

MULTI-MER PEPTIDES DERIVED FROM HEPATITIS C VIRUS ENVELOPE PROTEINS FOR DIAGNOSTIC USE AND VACCINATION PURPOSES

This is a continuation of PCT application PCT/EP98/07105, filed 6 Nov. 1998, the entire content of which is hereby incorporated by reference in this application.

FIELD OF THE INVENTION

The present invention relates to multi-mer peptides derived from hepatitis C virus envelope proteins which react with the majority of anti-HCV antibodies present in patient sera. Consequently, the present invention relates to the usage of the latter peptides to diagnose, and to vaccinate against, an infection with hepatitis C virus.

BACKGROUND OF THE INVENTION

Hepatitis C virus (HCV) infection is a major health problem in both developed and developing countries. It is estimated that about 1 to 5% of the world population is affected by the virus, amounting up to 175 million chronic infections worldwide. HCV infection appears to be the most important cause of transfusion-associated hepatitis and frequently progresses to chronic liver damage. Moreover, there is evidence implicating HCV in induction of hepatocellular carcinoma. Consequently, the demand for reliable diagnostic methods and effective therapeutic agents is high. There is also an urgent need to characterize new epitopes which can be used in the design of effective vaccines against hepatitis C.

HCV is a positive stranded RNA virus of about 9,8 kilobases which code for at least three structural and at least six non-structural proteins. The structural proteins have not yet been functionally assigned, but are thought to consist of a single core protein and two envelope proteins E1 and E2. The E1 protein consists of 192 amino acids and contains 5 to 6 N-glycosylation sites, depending on the HCV genotype, whereas the E2 protein consists of 363 to 370 amino acids and contains up to 11 N-glycosylation sites, depending on the HCV genotype (for review see Maertens and Stuyver, 1997).

The E1 and E2 proteins are currently not included in HCV antibody (Ab) assays, primarily because of their complex conformational structures which require expression in mammalian cells as well as non-denaturing purification techniques. Indeed, after expression of E2 in *Escherichia coli*, the reactivity of HCV sera with the recombinant protein ranged from 14 (Yokosuka et al., 1992) to 17% (Mita et al., 1992), whereas expression in eukaryotic systems yields reactivities of 13 to 97% (Inoue, 1992; Chien, 1993). Others demonstrated that the E1 protein expressed as a single protein from eukaryotic cells did not shown high reactivity with patient sera (from 6 to 60%; Kohara et al. (1992), Hsu et al. (1992), Chien et al. (1993)). We previously reported that high prevalences of Ab's to both of the purified recombinant E1 and E2 proteins, which were expressed in mammalian cells, could be found in sera from chronic hepatitis C patients (WO 96/04385 to Maertens et al.). In this regard, we also demonstrated that the majority of anti-E1 and anti-E2 antibodies in sera from HCV patients could not be mapped using 20-mer peptides (WO 96/04385 to Maertens et al.). Indeed, although all of the murine monoclonal Ab's against E1 could be mapped to reactivity with two 20-mer peptides, denoted as epitope A (amino acids (aa) 313–326) and epitope B (aa 208–224), at most 50% of patient sera reactive with recombinant proteins recognized epitope A and B. With regard to the E2 protein, only three out of twenty four murine monoclonal Ab's could be mapped using 20-mer peptides. These three Ab's were mapped to the hypervariable region I (HVR I) covered by peptide E2-67 (aa 394–413) and to a region covered by a peptide denoted E2-13B (aa 523–542). The remaining twenty-one Ab's could not be mapped using 20-mer peptides. The relative map positions of seven of these Ab's could be deduced from competition studies using recombinant E2 protein.

Taken together, it appears that anti-E1 and anti-E2 Ab's might be highly prevalent in sera of HCV patients. However, determining the presence of these Ab's is problematic due to the need to use eukaryotically expressed E1 and E2, which have to be purified using cumbersome non-denaturing techniques. As an alternative, chemically synthesized 20-mer peptides derived from the E1 and/or E2 proteins were produced. However, these synthesized 20-mer peptides were not able to recognize the anti-E1 and anti-2 Ab's in sera from HCV patients.

There is thus a need to design alternative methods to screen for HCV envelope Ab's.

AIMS OF THE INVENTION

It is clear from the literature cited above that the E1 and E2 proteins probably have complex conformational structures which are essential for recognizing (and binding to) the anti-E1 and anti-E2 Ab's in sera from HCV patients. This could explain why prokaryotically expressed complete or near-complete E1 and E2 proteins, which might be malfolded due to the lack of glycosylations, relevant chaperones or correct cysteine bridges, and 20-mer peptides, which might be unable to mimic a complex conformational structure, are not able to recognize these Ab's.

The present invention relates to the surprising finding that multi-mer peptides (eg 30- to 45-mer peptides) are able to recognize the majority of anti-E1 and anti-E2 Ab's in sera from HCV patients. It should be clear that this is a surprising finding because there is no guidance which would suggest that 30- to 45-mer peptides derived from E1 and E2 would acquire proper folding and would efficiently recognize the majority of HCV envelope Ab's. In contrast, one would assume that the chance that multi-mer peptides malfold would be as great, or even greater, than the chance that prokaryotically expressed complete proteins malfold as is suggested above. In the case of the HCV NS3 protein for example, which reacts with more than 90% of patient samples as expressed from *E. coli*, 20–50 mer peptides only react very weakly.

Therefore, the present invention aims at providing a peptide of more than 20 contiguous amino acids derived from the envelope region of HCV-related viruses which binds and recognizes anti-HCV-related virus antibodies. HCV-related viruses, including HCV, GBV-B virus, GBV-A virus and GBV-C (HGV or hepatitis G virus), are a division of the Flaviviruses, which further comprise Dengue virus, Yellow fever virus, Pestiviruses such as Classical Swine Fever Virus and Bovine Viral Diarrhea Virus (Wengler, 1991).

More specifically, the present invention aims at providing a peptide which binds and recognizes an anti-HCV antibody or an anti-HGV antibody present in a sample of body fluid and which is chosen from the group consisting of the sequences as represented in SEQ ID NOs 1 to 38 (see Table 1) or a functionally equivalent variant or fragment thereof.

In this respect, the present invention aims specifically at providing a peptide as described above, wherein said anti- HCV antibody present in a sample of body fluid is an anti-HCV-E1 antibody or an anti-HCV-E2 antibody.

The present invention thus aims also at providing a peptide as described above, wherein said anti-HGV antibody present in a sample of body fluid is an anti-HGV-E1 antibody or an anti-HGV-E2 antibody.

Moreover, the present invention aims at providing a peptide as described above, wherein said peptide is synthesized chemically or is synthesized using recombinant DNA techniques.

The present invention also aims at providing a peptide as described above, wherein said peptide is biotinylated or contains cysteine bridges.

Furthermore, the present invention aims at providing any combination of peptides as described above, as well as compositions containing said combination of peptides or peptides as described above.

In addition, the present invention aims at providing a method for diagnosing exposure to or infection by HCV-related viruses comprising contacting anti-HCV-related virus antibodies within a sample of body fluid with a peptide as described above or with a combination of peptides as described above, determining the binding of anti-HCV-related virus antibodies within a sample of body fluid with a peptide as described above or with a combination of peptides as described above.

In addition, the present invention aims at providing an assay kit for detecting the presence of anti-HCV-related virus antibodies within a sample of body fluid comprising a solid support, a peptide as described above or a combination of peptides as described above, appropriate markers which allow to determine the complexes formed between anti-HCV-related virus antibodies within a sample of body fluid with a peptide as described above or a combination of peptides as described above.

In addition, the present invention aims at providing a bioassay for identifying compounds which modulate the interaction between a peptide and an anti-HCV-related virus antibody, said bioassay comprising contacting anti-HCV-related virus antibodies with a peptide as described above or a combination of peptides as described above, determining the binding of anti-HCV-related virus antibodies with a peptide as described above or a combination of peptides as described above, adding a modulator (ie a compound which is able to modulate the interaction between an envelope protein and an anti-HCV-related virus antibody) or a combination of modulators to the contacted anti-HCV-related virus antibodies with a peptide as described above or a combination of peptides as described above, determining the modulation of binding of anti-HCV-related virus antibodies with a peptide as described above or a combination of peptides as described above In addition, the present invention aims at providing a bioassay for identifying compounds which modulate the interaction between a peptide and an anti-HCV-related virus antibody, said bioassay comprising determining the binding of anti-HCV-related virus antibodies with a peptide as described above or a combination of peptides as described above, contacting a modulator with a peptide as described above or a combination of peptides as described above, adding anti-HCV-related virus antibodies to the contacted modulator with the peptide as described above or a combination of peptides as described above, determining the modulation of binding between anti-HCV-related virus antibodies with a peptide as described above or a combination of peptides as described above.

Moreover, the present invention aims at providing a modulator, a composition containing a modulator, or a combination of modulators when produced by the bioassay as described above or when identified by the above-described bioassays.

Moreover, the present invention aims at providing a composition comprising a plasmid vector comprising a nucleotide sequence encoding a peptide as described above, or a modulator as described above, operably linked to transcription regulatory elements.

Moreover, the present invention aims at providing a composition as described above for use to vaccinate or therapeutically treat humans against infection with HCV-related virus or any mutated strain thereof.

Moreover, it is an aim of the present invention to provide an antibody, more particularly a monoclonal antibody, characterized in that it specifically recognizes an HCV-related virus polypeptide as described above. Finally, it is an aim of the present invention to provide a method to immunize humans against infection with HCV-related virus or any mutated strain thereof, comprising the use of a peptide as described above or a combination of peptides as described above.

All the aims of the present invention are considered to have been met by the embodiments as set out below. Other advantages and features of the instant invention will be evident from the following claims and detailed description.

BRIEF DESCRIPTION OF TABLES AND DRAWINGS

Table 1 provides information on the envelope protein and the HCV genotype from which the peptides of the present invention are derived. This table also provides the name, the amino acid sequence, the position within the envelope proteins and the sequence identity (SEQ ID) of the peptides of the present invention.

Table 2 shows ELISA results (in mOD) of reactivities of multimer peptides and recombinant E2 with 60 HCV positive samples and 4 control samples.

Table 3 shows the analysis for E1 antibodies of 23 sera from responders to interferon treatment.

Table 4 shows the analysis of E2 antibodies of 23 sera from responders to interferon treatment.

Table 5 shows the monitoring of disease over time by measuring antibodies to the HCV E1 and E2 regions in 18 patients.

Table 6 indicates the reactivity of HGV (Hepatitis G virus) RNA positive sera with the HGV E1 peptide V1V2.

FIG. 1 demonstrates the positions of the multi-mer peptides of the present invention relative to the conserved and variable regions of the E1 envelope protein of HCV (HVR= hypervariable regions; V=variable regions; C=conserved regions; HR=hydrophobic region; SA=signal anchor domain; Y=glycosylation; ▇ =cysteine).

Figure 2:
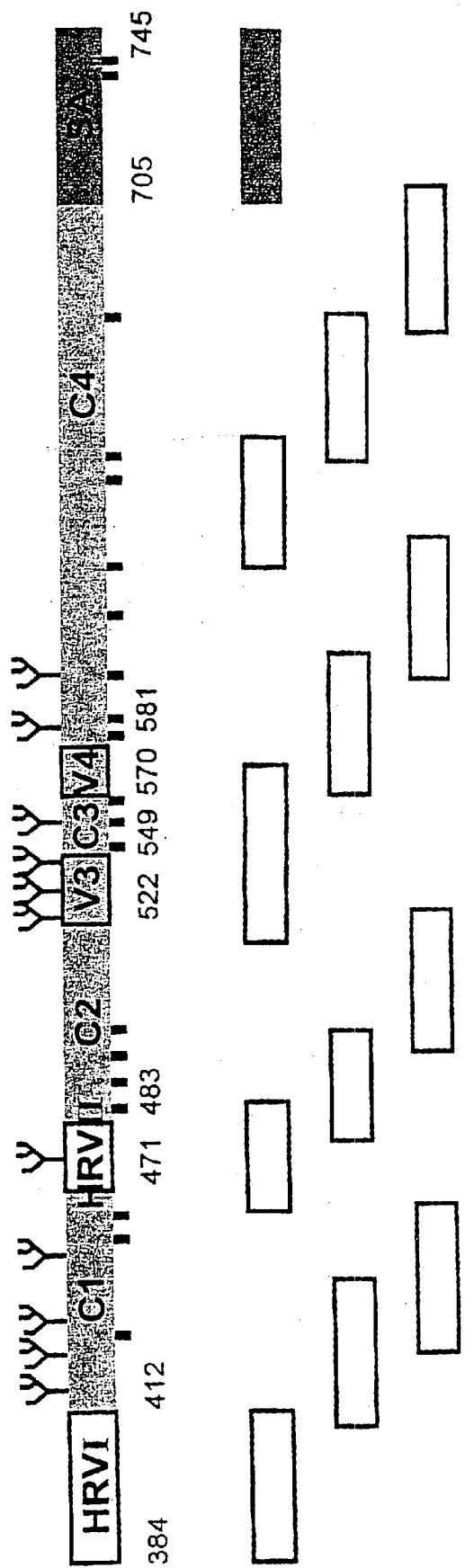

FIG. 2 demonstrates the positions of the multi-mer peptides of the present invention relative to the conserved and variable regions of the E2 envelope protein of HCV (HVR= hypervariable regions; V=variable regions; C=conserved regions; SA=signal anchor domain; Y=glycosylation; ▇ =cysteine).

Figure 3:
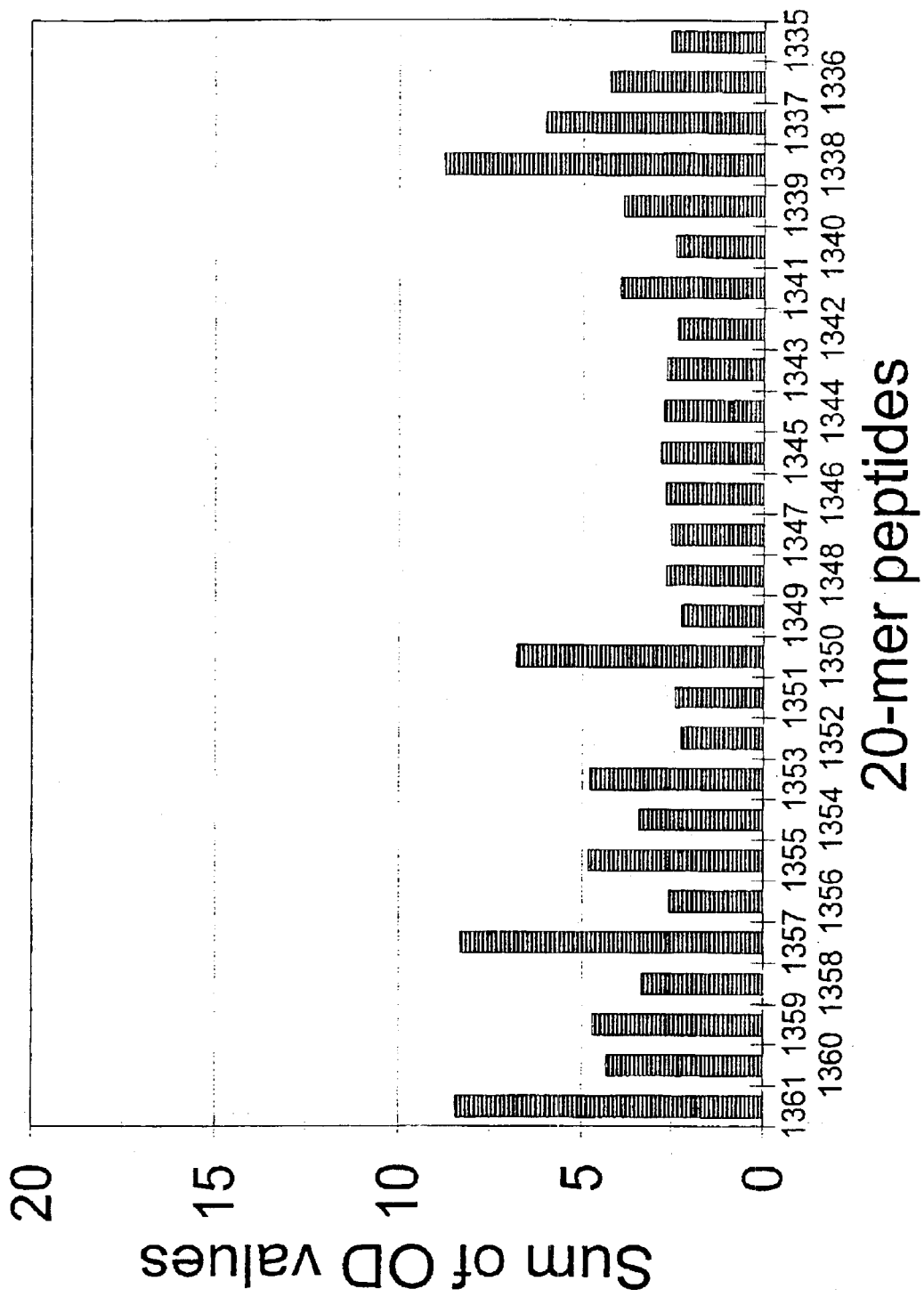

FIG. 3 shows the reactivity of 20-mer E2 peptides. The OD values of serum samples from patients with chronic active hepatitis C were added and plotted against the different peptides.

Figure 4:
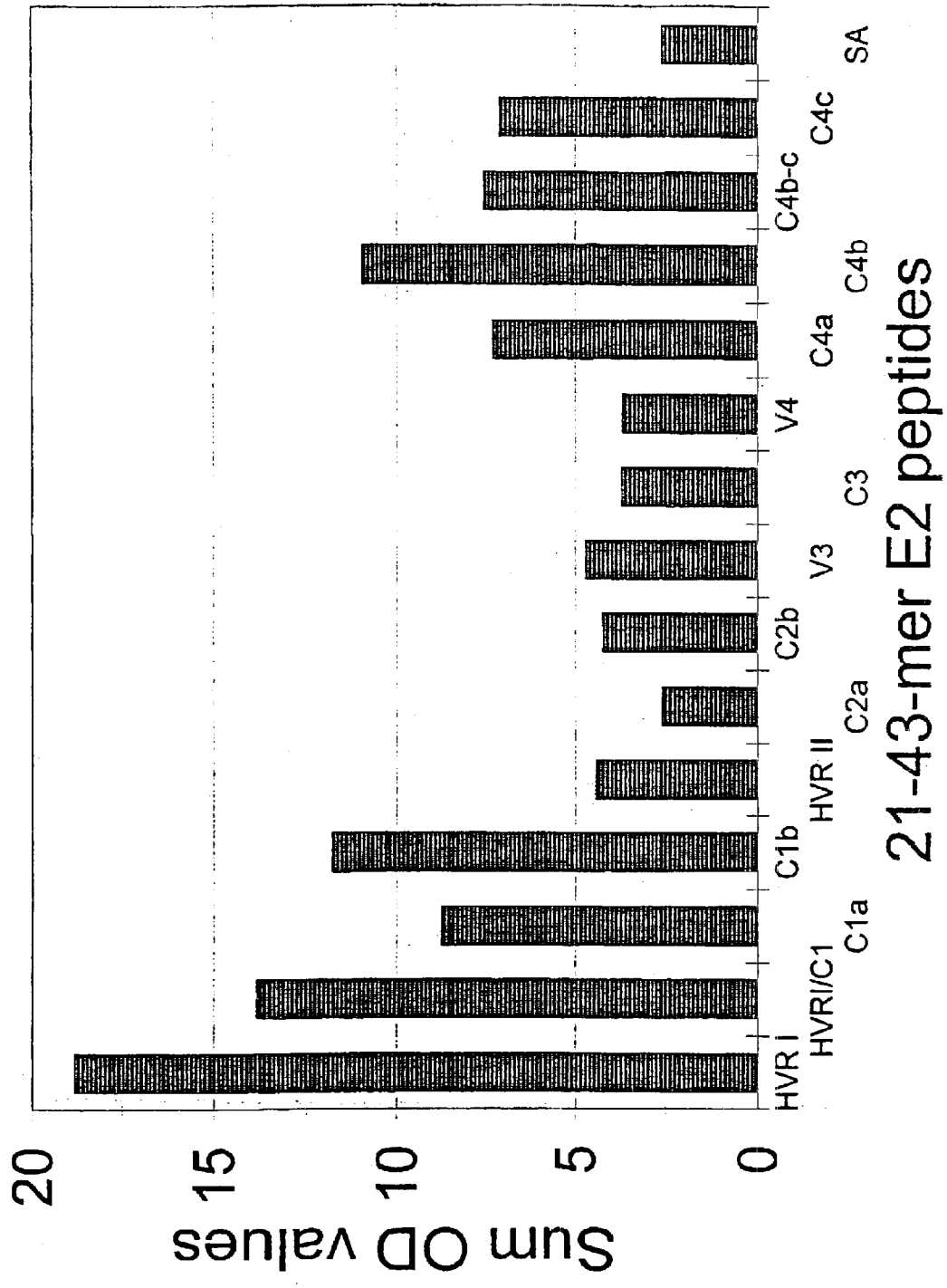

FIG. 4 shows the reactivity of mulit-mer E2 peptides. The OD values of the samples were added and plotted against the different peptides. The samples were identical as used for FIG. 3.

DETAILED DESCRIPTION OF THE INVENTION

The invention described herein draws on previously published work and pending patent applications. By way of example, such work consists of scientific papers, patents or pending patent applications. All these publications and applications, cited previously or below are hereby incorporated by reference.

The present invention is based on the finding that multimer peptides, as of a certain length, derived from the envelope proteins of HCV-related viruses, eg HCV and HGV, recognize and bind anti-HCV-related virus antibodies, eg anti-HCV antibodies and anti-HGV antibodies, respectively. Therefore, the present invention provides a peptide of more than 20contiguous amino acids derived from the envelope region of HCV-related viruses which binds and recognizes anti-HCV-related virus antibodies.

HCV-related viruses include, but are not limited to HCV, GBV-B virus, GBV-A virus and GBV-C virus (HGV or hepatitis G virus)(Linnen et al., 1996). HCV constitutes a genus within the Flaviviridae, and is closely related to hepatitis G virus (26.8% at the amino acid level). The term "envelope region" of HCV-related viruses is a well-known region by a person skilled in the art (Wengler, 1991), and comprises the E1 protein as well as the E2 protein, which was previously called non-structural protein 1 (NS1) or E2/NS1.

Furthermore, the present invention relates to a peptide, which binds and recognizes an anti-HCV antibody or an anti-HGV antibody present in a sample of body fluid, and which is chosen from the group consisting of the sequences as represented in SEQ ID 1 to 38 (see Table 1) or a functionally equivalent variant or fragment thereof.

The present invention relates also to a peptide as described above, wherein said anti-HCV antibody or said anti-HGV antibody present in a sample of body fluid is an anti-HCV-E1 or anti-HCV-E2 antibody, or an anti-HGV-E1 or anti-HGV-E2 antibody, respectively.

The term "a peptide" refers to a polymer of amino acids (aa's) derived (i.e. containing less aa's) from the well-known HCV-related virus envelope proteins E1 and E2 (Linnen et al., 1996, Maertens and Stuyver, 1997), which binds anti-HCV-related virus antibodies. The term "a peptide" refers in particular to a polymer of aa's derived from HCV envelope proteins E1 and E2, which binds anti-HCV antibodies, or from HGV envelope proteins E1 and E2, which binds anti-HGV antibodies.

The terms "peptide", "polypeptide" and "protein" are used interchangeably herein. The term "an anti-HCV-related virus antibody" refers to any polyclonal or monoclonal antibody binding to a HCV-related virus particle or any molecule derived from said viral particle. More particularly, the term "an anti-HCV-related virus antibody" refers to antibodies binding to the natural, recombinant or synthetic E1 and/or E2 proteins derived from HCV or HGV proteins (anti-HCV-E1 or anti-HCV-E2 antibody, or anti-HGV-E1 or anti-HGV-E2 antibody, respectively).

The term "monoclonal antibody" used herein refers to an antibody composition having a homogeneous antibody population. The term is not limiting regarding the species or source of the antibody, nor is it intended to be limited by the manner in which it is made.

In addition, the term "antibody" also refers to humanized antibodies in which at least a portion of the framework regions of an immunoglobulin are derived from human immunoglobulin sequences and single chain antibodies as described in U.S. Pat. No. 4,946,778 and to fragments of antibodies such as $F_{ab}$, $F_{(ab)2}$, $F_v$, and other fragments which retain the antigen binding function and specificity of the parent antibody.

The term "a sample of body fluid" as used herein refers to a fluid obtained from an organism, such as serum, plasma, saliva, gastric secretions, mucus, spinal cord fluid, and the like.

The term "the group consisting of the sequences as represented in SEQ ID NOs 1 to 38" as used herein refers to thirty-eight peptides shown in Table 1 of the present application. In this table, it is indicated:

- in the column named "protein" from which HCV envelope protein the peptide is derived, but for the envelope protein of HGV, which is denoted E1(HGV),
- in the column named "genotype" the HCV genotype from which the envelope protein is derived, and thus the peptide is derived, except for HGV which was not determined (ND),
- in the column named "peptide" the assignment of the peptide region.
- the aa sequence of the peptide and,
- in the column named "position", the well-known (Maertens and Stuyver, 1997) aa position of the peptides within the HCV envelope proteins. Note that the position for the E1 envelope protein is not determined, which is denoted as "ND".

The term "functionally equivalent" as used in "functionally equivalent variant or fragment thereof" refers to variants and fragments of the peptides represented by SEQ ID 1 to 38, which bind anti-HCV-related virus antibodies. The term "variant or fragment" as used in "functionally equivalent variant or fragment thereof" refers to any variant or any fragment of the peptides represented by SEQ ID 1 to 38. Furthermore, the latter terms do not refer to, nor do they exclude, post-translational modifications of the peptides represented by SEQ ID 1 to 38 such as glycosylation, acetylation, phosphorylation, modifications with fatty acids and the like. Included within the definition are, for example, peptides containing one or more analogues of an aa (including unnatural aa's), peptides with substituted linkages, mutated versions or natural sequence variations of the peptides (for example corresponding to the genotypes HCV, as described in WO 94/12670 to Maertens et al.), peptides containing disulfide bounds between cysteine residues, or other cysteine modifications, biotinylated peptides, as well as other modifications known in the art. Modification of the structure of the polypeptides can be for such objectives as increasing therapeutic or prophylactic efficacy, stability (e.g. ex vivo shelf life and in vivo resistance to proteolytic degradation), or post-translational modifications (e.g. to alter the phosphorylation pattern of protein). Such modified peptides, when designed to retain at least one activity of the naturally-occurring form of the protein are considered functional equivalents of the polypeptides described in more detail herein. Such modified peptides can be produced, for instance, by amino acid substitution, deletion, or addition. For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids can be divided into four families: (1) acidic: aspartate, glutamate; (2) basic: lysine, arginine, histidine; (3) nonpolar: alanine, valine, leucine, isoleucine, proline, phenylalanine, methionine, tryptophan; and (4) uncharged polar: glycine, asparagine, glutamine, cysteine, serine, threonine, tyrosine. In similar fashion, the amino acid repertoire can be grouped as (1) acidic: aspartate, glutamate; (2) basic: lysin, arginine histidine, (3) aliphatic: glycine, alanine, valine, leucine, isoleucine, serine, threonine, with serine and threonine optionally be grouped separately as aliphatic-hydroxyl; (4) aromatic: phenylalanine, tyrosine, tryptophan; (5) amide: asparagine, glutamine; and (6) sulfur-containing: cysteine and methionine (see, for example, Biochemistry, 2nd ed., Ed. by L. Stryer, W H Freeman and Co.: 1981). Whether a change in the amino acid sequence of a peptide results in a functional homologue (e.g. functional in the sense that the resulting polypeptide mimics the wild-type form) can be readily determined by assessing the ability of the variant peptide to produce a response in e.g. ELISAs in a fashion similar to the wild-type protein, or to competitively inhibit such a response. Polypeptides in which more than one replacement has been introduced can be readily tested in the same manner.

It should also be clear that the region of a peptide represented by SEQ ID 1 to 38 which bind to an antibody (the so-called epitope) need not to be composed of a contiguous aa sequence.

In this regard, the term "fragment" includes any fragment which comprises these non-contiguous binding regions or parts thereof. In other words, fragments which include these binding regions may be separated by a linker, which is not a functional part of the epitope. This linker does not need to be an amino acid sequence, but can be any molecule, eg organic or inorganic, that allows the formation of the desired epitope by two or more fragments.

Moreover, it should be clear that the variants and fragments of SEQ ID NOs 1 to 5, 7 to 9, and 18 as used herein include peptides having a length of at least 21 aa's, or 22 aa's, or 23 aa's, or 24 aa's, or 25 aa's, or 26 aa's, or 27 aa's, or 28 aa's, or 29 aa's, or 30 aa's, or 31 aa's, or 32 aa's, or 33 aa's, or 34 aa's. Moreover, it should be clear that the variants and fragments of SEQ ID NO 6 as used herein include to peptides having a length of at least 21 aa's, or 22 aa's, or 23 aa's. Moreover, it should be clear that the variants and fragments of SEQ ID NO 10 as used herein include to peptides having a length of at least 21 aa's, or 22 aa's, or 23 aa's, or 24 aa's, or 25 aa's, or 26 aa's, or 27 aa's, or 28 aa's. Moreover, it should be clear that the variants and fragments of SEQ ID NOs 11, 15, 21, 34 as used herein include to peptides having a length of at least 21 aa's, or 22 aa's, or 23 aa's, or 24 aa's, or 25 aa's, or 26 aa's, or 27 aa's, or 28 aa's, or 29 aa's, or 30 aa's, or 31 aa's, or 32 aa's, or 33 aa's. Moreover, it should be clear that the variants and fragments of SEQ ID NOs 12, 24 or 32 as used herein include to peptides having a length of at least 21 aa's, or 22 aa's, or 23 aa's, or 24 aa's,or 25 aa's, or 26 aa's, or 27 aa's, or 28 aa's, or 29 aa's, or 30 aa's, or 31 aa's, or 32 aa's, or 33 aa's, or 34 aa's, or 35 aa's. Moreover, it should be clear that the variants and fragments of SEQ ID NOs 13, 22, or 34 used herein include to peptides having a length of at least 21 aa's, or 22 aa's, or 23 aa's, or 24 aa's, or 25 aa's, or 26 aa's, or 27 aa's, or 28 aa's, or 29 aa's, or 30 aa's. Moreover, it should be that clear the variants and fragments of SEQ ID NO 16 as used herein include to peptides having a length of at least 21 aa's, or 22 aa's, or 23 aa's, or 24 aa's, or 25 aa's, or 26 aa's, or 27 aa's, or 28 aa's, or 29 aa's, or 30 aa's, or 31 aa's, or 32 aa's, or 33 aa's, or 34 aa's, 35 aa's, or 36 aa's, or 37 aa's, or 38 aa's, or 39 aa's, or 40 aa's. Moreover, it should be clear that the variants and fragments of SEQ ID NO 17 as used herein refers to peptides having a length of at least 21 aa's, or 22 aa's, or 23 aa's, or 24 aa's, or 25 aa's, or 26 aa's, or 27 aa's, or 28 aa's, or 29 aa's, or 30 aa's, or 31 aa's. Moreover, it should be clear that the variants and fragments of SEQ ID NO 19 as used herein refers to peptides having a length of at least 21 aa's, or 22 aa's, or 23 aa's, or 24 aa's, or 25 aa's, or 26 aa's, or 27 aa's, or 28 aa's, or 29 aa's, or 30 aa's, or 31 aa's, or 32 aa's, or 33 aa's, or 34 aa's, 35 aa's, or 36 aa's, or 37 aa's. Moreover, it should be clear that the variants and fragments of SEQ ID NOs 20 and 30 as used herein include to peptides having a length of at least 21 aa's, or 22 aa's, or 23 aa's, or 24 aa's, or 25 aa's, or 26 aa's, or 27 aa's. Moreover, it should be clear that the variants and fragments of SEQ ID NO 23 as used herein include to peptides having a length of at least 21 aa's, or 22 aa's, or 23 aa's, or 24 aa's, or 25 aa's, or 26 aa's, or 27 aa's, or 28 aa's, or 29 aa's, or 30 aa's, or 31 aa's, or 32 aa's, or 33 aa's, or 34 aa's, 35 aa's, or 36 aa's, or 37 aa's, or 38 aa's, or 39 aa's, or 40 aa's, or 41 aa's, or 42 aa's, or 43 aa's. Moreover, it should be clear that the variants and fragments of SEQ ID NOs 25 or 29 as used herein include peptides having a length of at least 21 aa's, or 22 aa's, or 23 aa's, or 24 aa's. Moreover, it should be clear that the variants and fragments of SEQ ID NO 26 as used herein include peptides having a length of at least 21 aa's, or 22 aa's, or 23 aa's, or 24 aa's, or 25 aa's, or 26 aa's, or 27 aa's, or 28 aa's, or 29 aa's. Moreover, it should be clear that the variants and fragments of SEQ ID NO 27 as used herein include peptides having a length of at least 21 aa's, or 22 aa's, or 23 aa's, or 24 aa's, or 25 aa's, or 26 aa's, or 27 aa's, or 28 aa's, or 29 aa's, or 30 aa's, or 31 aa's, or 32 aa's, or 33 aa's, or 34 aa's, 35 aa's, or 36aa's, or 37 aa's, or 38 aa's, or 39 aa's, or 40 aa's, or 41 aa's, or 42 aa's, or 43 aa's, or 44 aa's. Moreover, it should be clear that the variants and fragments of SEQ ID NO 28 or 31 as used herein include peptides having a length of at least 21 aa's, or 22 aa's, or 23 aa's, or 24 aa's, or 25 aa's, or 26 aa's, or 27 aa's, or 28 aa's, or 29 aa's, or 30 aa's, or 31 aa's, or 32 aa's. Moreover, it should be clear that the variants and fragments of SEQ ID NO 33 as used herein include peptides having a length of at least 21 aa's, or 22 aa's, or 23 aa's, or 24 aa's, or 25 aa's, or 26 aa's, or 27 aa's, or 28 aa's, or 29 aa's, or 30 aa's, or 31 aa's, or 32 aa's, or 33 aa's, or 34 aa's, 35 aa's, or 36 aa's, or 37 aa's, or 38 aa's, or 39 aa's, or 40 aa's, or 41 aa's. Moreover, it should be clear that the variants and fragments of SEQ ID NOs 14 or 37 as used herein include peptides having a length of at least 21 aa's, or 22 aa's, or 23 aa's, or 24 aa's, or 25 aa's, or 26 aa's, or 27 aa's, or 28 aa's, or 29 aa's, or 30 aa's, or 31 aa's, or 32 aa's, or 33 aa's, or 34 aa's, 35 aa's, or 36 aa's, or 37 aa's, or 38 aa's, or 39 aa's.

In addition, it shall be appreciated by the person skilled in the art that the amino acid regions of the peptides, which are disclosed in the present invention and that bind anti-HCV antibodies, can be delineated in more detail by experimentation.

In addition, it should be clear that the variants and fragments of the peptides represented by SEQ ID 1 to 38, as herein described, can be prepared by any method known in the art such as classical chemical synthesis, as described by Houbenweyl (1974) and Atherton & Shepard (1989), or by means of recombinant DNA techniques as described by eg Maniatis et al. (1982), or Sambrook et al. (1989).

Similarly, it should be clear that also the peptides represented by SEQ ID 1 to 38 of the present invention can be prepared by any method known in the art and more particularly by means of classical chemical synthesis, as described by Houbenweyl (1974) and Atherton & Shepard (1989), or by means of recombinant DNA techniques such as described by eg Maniatis et al. (1982), or Sambrook et al. (1989).

The present invention further relates to the peptides represented by SEQ ID 1 to 38 and functionally equivalent variants or fragments thereof, all as defined above, which are biotinylated or contain cysteine bridges. Biotinylated peptides can be obtained by any method known in the art, such as the one described in WO93/18054 to De Leys. Methods for obtaining peptides containing inter- and/or intramolecular cysteine bridges are extensively described in WO 96/13590 to Maertens & Stuyver.

The present invention also relates to any combination of peptides represented by SEQ ID 1 to 38 and functionally equivalent variants or fragments thereof as defined above. The terms "any combination" refers to any possible mixture of above-described peptides or any possible linkage (covalently or otherwise) between above-described peptides. Examples of the latter peptide combinations are simple mixtures, homo- or hetero-branched peptides, combinations of biotinylated peptides presented on streptavidin, avidin or neutravidin, chemically cross-linked peptides with or without spacer, condensed peptides and recombinantly produced peptides.

The present invention relates also an antibody, more particularly a monoclonal antibody, characterized in that it specifically recognizes an HCV-related virus polypeptide as described above.

The present invention also relates to a method for diagnosing exposure to or infection by HCV-related viruses comprising contacting anti-HCV-related virus antibodies within a sample of body fluid with a peptide as described above or with a combination of peptides as described above, and, determining the binding of anti-HCV-related virus antibodies within a sample of body fluid with a peptide as described above or with a combination of peptides as described above. As used herein, the term "a method for diagnosing" refers to any immunoassay known in the art such as assays which utilize biotin and avidin or streptavidin, ELISAs and immunoprecipitation and agglutination assays. A detailed description of these assays is given in WO 96/13590 to Maertens & Stuyver.

In this regard, the present invention also relates to an assay kit for detecting the presence of anti-HCV-related virus antibodies comprising a solid support, a peptide as described above or a functionally equivalent variant or fragment thereof, or combination of peptides as described above, and appropriate markers which allow to determine the complexes formed between anti-HCV-related virus antibodies within a sample of body fluid with a peptide as described above, or a functionally equivalent variant or fragment thereof, or combination of peptides as described above.

The term "a solid support" refers to any solid support known in the art. Similarly, the term "appropriate markers" refers to any marker known in the art. It should also be clear that the term "a method for diagnosing" encompasses screening, detection, confirmation, monitoring and serotyping methods.

The present invention further pertains to a bioassay for identifying compounds which modulate the binding between a peptide and an anti-HCV-related virus antibody, comprising contacting anti-HCV-related virus antibodies with a peptide as described above, or a combination of peptides as described above, and determining the binding of anti-HCV-related virus antibodies with a peptide as described above, or a combination of peptides as described above, adding a modulator or a combination of modulators to the contacted anti-HCV-related virus antibodies with a peptide as described above, or a combination of peptides as described above, and finally determining the modulation of binding of anti-HCV-related virus antibodies with a peptide as described above, or a combination of peptides as described above.

In another embodiment the present invention features a bioassay for identifying compounds which modulate the binding between a peptide and an anti-HCV-related virus antibody, comprising determining the binding of anti-HCV-related virus antibodies with a peptide as described above, or a combination of peptides as described above, contacting a modulator with a peptide as described above, or a combination of peptides as described above, adding anti-HCV-related virus antibodies to the contacted modulator with a peptide as described above, or a combination of peptides as described above, determining the modulation of binding of anti-HCV-related virus antibodies with a peptide as described above, or a combination of peptides as described above.

The term "compound" as used herein refers to a composition, which has a molecular weight of less than about 25 KDa, preferably less than 10 KDa, and most preferably less than 5 KDa. Compounds can be nucleic acids, peptides, polypeptides, peptidomimeties, carbohydrates, lipids or other organic or inorganic molecules, or antibodies which may be generated by the host itself upon vaccination. The term "binding" as used herein indicates that a peptide as described above is physically connected to, and interacts with antibodies. Binding of the peptide to the antibody can be demonstrated by any method or assay known in the art such as binding-, ELISA, and RIA-type of assays or competition assays (eg see Examples section and Current protocols in immunology).

The terms "modulation" or "modulate" as used herein refer to both upregulation (i.e., activation or stimulation (e.g., by agonizing or potentiating)) and downregulation (i.e. inhibition or suppression (e.g. by antagonizing, decreasing or inhibiting) of the binding between a peptide and an anti-HCV antibody.

The term "modulator" as used herein refer to the ability of a compound as described above to modulate as described above.

The term "peptidomimetics" as used herein refers to molecules which can be manufactured and which mimic those residues of peptides which modulate the interaction of the antibody with the peptide as described above. For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R Marshall ed., ESCOM Publisher: Leiden, Netherlands, 1988), PNA, substituted gamma lactam rings (Garvey et al. in Peptides: Chemistry and Biology, G. R. Marshall ed., ESCOM Publisher: Leiden, Netherlands, 1988), ketomethylene pseudopeptides (Ewenson et al. (1986) J Med Chem 29:295: and Ewenson et al. in Peptides: Structure and Function (Proceedings of the 9th American Peptide Symposium) Pierce Chemical Co. Rockland, Ill., 1985), β-turn dipeptide cores (Nagai et al. (1985) Tetrahedron Lett 26:647; and Sato et al. (1986) J Chem Soc Perkin Trans 1:1231), and β-aminoalcohols (Gordon et al. (1985) Biochem Biophys Res Commun, 126:419; and Dann et al. (1986) Biochem Biophys Res Commun 134:71).

The present invention pertains to a modulator produced by a bioassay as described above.

The present invention pertains also to a modulator for the interaction between a peptide and an anti-HCV-related virus antibody, when said modulators are identified by a bioassay as described above.

The present invention features a composition comprising as an active substance a peptide as described above or a combination of peptides as described above.

The present invention features also a composition comprising as an active substance a modulator as described above or a combination of modulators as described above.

In another embodiment, the present invention relates to a composition comprising a plasmid vector comprising a nucleotide sequence encoding a peptide as described above, operably linked to transcription regulatory elements. Upon introduction in a human tissue said plasmid vector induces the expression in vivo, of the nucleotide sequence thereby producing the encoded protein. If said protein elicits an immunogenic response it is referred to as a DNA vaccine. It is readily apparent to those skilled in the art that variations or derivatives of the nucleotide sequence can be produced which alter the nucleotide sequence. The altered polynucleotide may have an altered nucleic sequence, yet still encodes a protein as described above, and which reacts with anti-HCV-related virus antibodies, and is considered a to be functional equivalent.

In a preferred embodiment, the present invention relates to a composition as described herein for use as to vaccinate humans against infection with HCV-related virus or any mutated strain thereof.

In another preferred embodiment, the present invention relates to a composition as described herein for use as to therapeutically treat humans against infection with HCV-related virus or any mutated strain thereof.

A composition of the present invention can be, as appropiate, any of the preparations described herein, including peptides, functionally equivalent variants or fragments thereof, a combination of peptides, or modulators (e.g. as identified in the bioassay provided herein). Specifically, the term "a composition" relates to an immunogenic composition capable of eliciting protection against HCV-related virus, in particular against HCV and/or HGV, whether partial or complete. The term "as an active substance" relates to the component of the vaccine composition which elicits protection against HCV-related viruses, in particular against HCV and/or HGV. An active substance (e.g. the peptides or the modulators of the present invention) can be used as such, in a biotinylated form (as explained in WO 93/18054) and/or complexed to *Neutralite Avidin* according to the manufacturer's instruction sheet (Molecular Probes Inc., Eugene, Oreg.).

It should also be noted that "a composition" comprises, in addition to an active substance, a suitable excipient, diluent, carrier and/or adjuvant which, by themselves, do not induce the production of antibodies harmful to the individual receiving the composition nor do they elicit protection. Suitable carriers are typically large slowly metabolized macromolecules such as proteins, polysaccharides, polylactic acids, polyglycolic acids, polymeric aa's, aa copolymers and inactive virus particles. Such carriers are well known to those skilled in the art. Preferred adjuvants to enhance effectiveness of the composition include, but are not limited to: aluminium hydroxide, aluminium in combination with 3-0-deacylated mononphosphoryl lipid A as described in WO 93/19780, aluminium phosphate as described in WO 93/24148, N-acetyl-muramyl-L-threonyl-D-isoglutamine as described in U.S. Pat. No. 4,606,918, N-acetyl-normuramyl-L-alanyl-D-isoglutamine,N-acetylmuramyl-L-alanyl-D-isoglutamyl-L-alanine2(1'2'dipalmitoyl-sn-glycero-3-hydroxyphosphoryloxy)ethylamine and RIBI (ImmunoChem Research Inc., Hamilton, Mont.), which may contain one or all of the following elements: monophosphoryl lipid A (detoxified endotoxin), trehalose-6,6-dimycolate, and cell wall skeleton (MPL+TDM+CWS) in a 2% squalene/Tween 86 emulsion. Any of the three components MPL, TDM or CWS may also be used alone or combined 2 by 2. Additionally, adjuvants such as Stimulon (Cambridge Bioscience, Worcester, Mass.), MF 57 (Chiron) or SAF-1 (Syntex) may be used,as well as adjuvants such as combinations between QS21 and 3-de-O-acetylated monophosphoryl lipid A (WO94/00153), or MF-59 (Chiron), or poly[di(carboxylatophenoxy)phosphazene] based adjuvants (Virus Research Institute), or blockcopolymer based adjuvants such as Optivax (Vaxcel) or Gammalnulin (Anutech), or Gerbu (Gerbu Biotechnik). Furthermore, Complete Freund's Adjuvant (CFA) and Incomplete Freund's Adjuvant (IFA) may be used for non-human applications and research purposes. "A composition" will further contain excipients and diluents, which are inherently non-toxic and non-therapeutic, such as water, saline, glycerol, ethanol, wetting or emulsifying agents, pH buffering substances, preservatives, and the like. Typically, a vaccine composition is prepared as an injectable, either as a liquid solution or suspension. Solid forms, suitable for solution on, or suspension in, liquid vehicles prior to injection may also be prepared. The preparation may also be emulsified or encapsulated in liposomes for enhancing adjuvant effect. The polypeptides may also be incorporated into Immune Stimulating Complexes together with saponins, for example Quil A (ISCOMS). Compositions, which can be used as a vaccine, comprise an immunologically effective amount of the polypeptides of the present invention and/or modulators, as well as any other of the above-mentioned components. "Immunologically effective amount" means that the administration of that amount to an individual, either in a single dosis or as part of a series, is effective for prevention or treatment. This amount varies depending upon the health and physical condition of the individual to be treated, the taxonomic group of the individual to be treated (e.g. non-human primate, primate, etc.), the capacity of the individual's immune system to mount an effective immune response, the degree of protection desired, the formulation of the vaccine, the treating's doctor assessment, the strain of the infecting HCV and other relevant factors. It is expected that the amount will fall in a relatively broad range that can be determined through routine trials. Usually, the amount will vary from 0.01 to 1000 $\mu$g/dose, more particularly from 0.1 to 100 $\mu$g/dose. Compositions, which can be used as a vaccine are conventionally administered parenterally, typically by injection, for example, subcutaneously or intramuscularly.

In the case of DNA vaccines, particular useful methods for eliciting an immune response include the coating of gold particles with the plasmid vector encoding the desired peptide, and injecting them under high pressure into the epidermis and/or dermis, eg by means of a device called gene gun (eg as produced by Powderject Vaccines, Madison, Wis., USA).

Additional formulations suitable for other methods of administration include oral formulations and suppositories. Dosage treatment may be a single dose schedule or a multiple dose schedule. The vaccine may be administered in conjunction with other immunoregulatory agents. It should be noted that a vaccine may also be useful for treatment of an individual, in which case it is used as a to "therapeutically treat humans".

As used herein, a "plasmid vector" refers to a nucleic acid molecule capable of transporting another nucleic acid to which it has been linked. Preferred vectors are those capable of autonomous replication and/or expression of nucleic acids to which they have been linked. In general, but not limited to those, plasmid vectors are circular double stranded DNA loops which, in their vector form, are not bound to the chromosome. For expression purposes, promoters are required. For DNA vaccination, a very suitable promoter is the Major Immediate Early (MIE) of human cytomegalovirus.

As used herein, a "nucleotide sequence" refers to polynucleotides such as deoxyribonucleic acid (DNA), and, where appropriate, ribonucleic acid (RNA). The term should also be understood to include, as equivalents, analogs of either RNA or DNA made from nucleotide analogs, and single (sense or antisense) and double-stranded polynucleotides.

As used herein, the term "transcription regulatory elements" refers to a nucleotide sequence which contains essential regulatory elements, ie such that upon introduction into a living vertebrate cell it is able to direct the cellular machinery to produce translation products encoded by the polynucleotide.

The term "operably linked" refers to a juxtaposition wherein the components are configured so as to perform their usual function. Thus, transcription regulatory elements operably linked to a nucleotide sequence are capable of effecting the expression of said nucleotide sequence. Those skilled in the art can appreciate that different transcriptional promoters, terminators, carrier vectors or specific gene sequences may be used succesfully.

Finally, the present invention provides a method to immunize humans against infection with HCV-related virus or any mutated strain thereof, comprising the use of a peptide as described above or a combination of peptides as described above.

The present invention will now be illustrated by reference to the following examples which set forth particularly advantageous embodiments. However, it should be noted that these embodiments are illustrative and can not be construed as to restrict the invention in any way.

EXAMPLES

Example 1

Synthesis of Multimer E1 and E2 Peptides

We aimed at synthesizing peptides which would display epitopes, similar to the ones present on E1 and E2 peptides expressed in mammalian cells. Since such epitopes do not seem to be present in E1 and E2 proteins expressed in *E. coli,* the design of such peptides was not an easy task. We first aligned E1 and E2 primary amino acid sequences of different HCV genotypes and delineated variable and constant domains. It was reasoned that these domains, or a combination of two or more of these domains might represent conformational domains, ie form or constitute independent conformational units. If displayed as 3D structure, these conformational domains may also contain conformational epitopes. The latter domains may therefore be able to adopt a native-like structure as is present in the envelope proteins when these envelope proteins are expressed in mammalian cells. In contrast, such structures are absent when the envelope proteins are expressed in prokaryotic cells, like *E. coli.*

The following domains were assigned: V1, V2, V3, V4, V5, V6=variable regions; C1, C2, C3, C4=conserved domains; HR=hydrophobic region; SA=signal anchor sequence; HVRI, HVRII=hypervariable regions of E2.

| Protein | Region | Amino acid position |
|---|---|---|
| E1 | V1 | 192–203 |
| | C1 | 204–217 |
| | V2 | 218–223 |
| | C2 | 224–229 |
| | V3 | 230–242 |
| | C3 | 243–247 |
| | V4 | 248–257 |
| | HR | 258–293 |
| | V5 | 294–303 |
| | C4 | 304–329 |
| | V6 | 330–342 |
| | SA | 343–383 |
| E2 | HVRI | 384–411 |
| | C1 | 412–470 |
| | HVRII | 471–482 |
| | C2 | 483–521 |
| | V3 | 522–548 |
| | C3 | 549–569 |
| | V4 | 570–580 |
| | C4 | 581–704 |
| | SA | 705–746 |

Based on these dormains of the BE11 subtype 1b isolate (SEQ ID 50 in PCT/EP 95/03031), we designed a series long peptides of 24 to 45 amino acids. For some extended domains of the envelope proteins more than one multimer peptide was synthesized in order to encompass the domain of interest. Table 1 gives an overview of the peptides with their respective amino acid positions; numbering starts from the first initiation codon of the HCV polyprotein. Peptides were synthesized using t-Boc technology as explained in detail in WO 93/18054.

Example 2

Reactivity of Multimer Peptides with E1 and E2 Antibodies in Patient Sera

A series of 60 randomly chosen samples from patients with chronic active hepatitis C were tested for reactivity with the multimer peptides. These samples did not show any notable reactivity with 20-mer peptides except for some 20-mer peptides derived from the HVRI. For comparison, reactivity with the hydrophylic ectodomain of E2, the recombinant E2h protein, was assayed (E2h extends from aa 384–708 and was cloned from SEQ ID NO 45, and expressed and purified as described in PCT/EP 95/03031). Peptides were coated onto streptavidin-coated plates (5 μg/ml) and antibodies in serum samples were left to react and detected using the reagents and procedures as described in the package insert of the INNOTEST HCV Ab III kit (Innogenetics, Gent, Belgium). Table 2 shows the results of the ELISA tests, in which a cutoff of 150 mOD was used. In this series, 5 sera did not show reactivity with the E2h protein, only one of these reacted with the HVRI peptide. Five out of 60 sera (8% e.g. sample 17758) only reacted with the E2h protein, 34 (57%) recognized HVRI, 24(40%) reacted with C1-a, 18 (30%) with C1-b, 21 (35%) with HVRII, 17 (28%) C2-a, 22 (37%) with C2-b, 18 (30%) with C3, 18 (30%) with C3', 17 (28%) with C3", 18 (30%) with V4, 22 (37%) with C-4, 21 (35%) with C4-a, 35 (58%) with C4-b, and 24 (40%) with C4-c. This experiment surprisingly learned that, while none of the samples recognized any of the 20-mer peptides, except for those derived from the HVRI, 50 out of 55 (91%) E2h reactive sera could be detected using the peptides of the present invention.

In a second series of 23 sera derived from chronic hepatitis C patients who were long-term responders to interferon-alpha treatment and 3 HCV infected chimpanzees, E1 and E2 antibodies were tested. Eighteen out of 23 samples (78%) reacted with recombinant E1s protein, expressed and purified from mammalian cells as described in PCT/EP95/03031. Nine samples (39%) reacted with the C4V6 region, another 9 (39%) with the V1V2 region, and 3 with V2V3 (Table 4). For comparative purposes peptide V5, ie SQLFTISPRRHETVQD (SEQ ID NO:39), is shown.

Different reactivities to E2 were observed (Table 4) as compared with the first series of samples. 21 samples (91%) reacted with E2h, with 13 (57%) reactive on HVRI, 9 (39%) with C1-a, 11 (48%) with C1-b, 1 with HVRII, C2-a, and C2-b each, 2 with C3, 3 with C4-a, 4 (17%) with C4-b, and 4 (17%) with C4-c. In this series of patients with a benign evolution of disease, the C1 region was more frequently recogniized and fewer antibodies to the C4 region were detected as compared to the series of samples obtained from patients with chronic active hepatitis. These results indicate that peptides from the C1, C2, and C4 regions may be particularly useful in monitoring the course on HCV-related virus disease. More specifically, antibodies to the C1 region may better neutralize HCV as compared to anti-C4 antibodies. The C1 domain may therefore be functionally important, eg exhibit receptor-binding activity. Neutralization of this region may therefore result in lesser activity of the disease and may lead to resolvement. The E2-C1 region may therefore be particularly useful in therapeutic interventions. It should also be noted that, once reactivity to a given domain is established, it can be further mapped to smaller peptides, e.g. reactivities of 1 chimpanzee serum to C3 could be mapped to smaller region of 25 amino acids (peptide C3").

Example 3

Monitoring of E1 and E2 Antibodies in Patients with Response to Interferon-alpha Therapy In Table 5, results of E2 antibody tests as described in example 2 are given for consecutive samples obtained from patients with response to interferon therapy. A decline in E2Ab, and to a larger extend E1Ab, has been described in PCT/EP 95/03031 in case of a long-term response to interferon treatment. Reactivities to several peptides of the present invention also show similar declining levels. Peculiar reactivities could sometimes be detected as exemplified in patient 2: upon the detection of reappearing virus, antibody responses to the (E1)V4V5 region and the (E2)HVRII region could be detected; these quickly disappeared simultaneously with viral clearance. (E1)V4V5 and (E2)HVRII may therefore be particularly useful peptides for disease monitoring, especially in treatment of disease. Other peptides such as (E2)C1 (example 2) and those shown in bold in Table 5 also seem to be useful for purposes such as monitoring. Table 2 also shows the presence of reactivity in patient 2 to a new peptide HVRI-C1, which overlaps the junction between HVRI and C1 (Table 2), in the absence of detectable reactivity to the HVRI or C1 peptides. Similarly, peptide C4-bc encompassing the region between C4-b and C4-c (Table 2), was tested in this series, and showed almost identical reactivities as compared to peptide C4-b. Therefore, it is possible that the C4-b epitope lies between aa 658 and 673, but surprisingly, the epitope does not seem to be presented in peptide SEQ ID 92 of PCT/EP 95/03031 (aa 655–674). The C4-c epitope is not present in C4-bc and therefore can be localized between aa 683 and 706.

Example 4

Application to Other Flaviviruses

To examine the applicability of the invention to envelope proteins of other HCV-related viruses, a peptide spanning the V1V2 region of the hepatitis G virus (GBV-C; Linnen et al., 1996; Simons et al., 1996) E1 region was synthesized, see also SEQ ID NO 38 (Table 1): NH2-THACRANGQYFLTNCCAPEDIGFCLEGGCLVALGGK-biotin.

So far, only reactivity to the complete HGV E2 protein seemed to be useful in the diagnosis of HGV. Peptide epitopes have not yet been described for GBV envelope proteins E1 or E2. Sixteen HGV RNA-positive sera were tested and 1 of these was reactive with the E1 peptide as shown in Table 6. Antibody reactivity to the recombinant HGV E2 protein (but not to HGV E2 peptides) is found in up to 15% of the European population, but cases with both HGV RNA and E2Ab are rare as they probably represent cases in which seroconversion and elimination of the virus is ongoing. Antibody reactivity to the HGV E1 protein has not yet been reported. Therefore, the HGV E1 peptide V1V2 is new and it may display higher reactivities in a series of HGV anti-E2 reactive sera. Using similar approaches as described in the present invention, HGV E2 peptides may also be synthesized. Multimer peptides from GBV-A or GBV-B can be synthesized in a similar approach as described for HCV and HGV.

Example 5

Reactivity of 20mer E2 Peptides Compared to Multimer E2Peptides

E2 peptides listed in Table 1 were analyzed for their reactivity with 32 serum samples from patients with chronic active hepatitis C. In addition, a series of overlapping 20-mer peptides were synthesized with exactly the same HCV subtype 1b sequence as used for the longer peptides and as shown in Table 1. The ELISA test used was the same as described in Example 2. FIGS. 3 and 4 show the reactivities of the series of 20-mer and longer peptides, respectively. Peptides with a sum of >5 (HVR I, HVR I/C1, C1a, C1b, C4a, C4b, C4c, C4b-c) were considered to be very useful for the detection of antibodies directed against E2. A total of six of these peptides (peptides C4b-c and C1a were not included as these peptides are almost entirely represented by other peptides) were combined together with 20-mer peptide 1350 (Table 1), which occasionally reacted with some patient sera. The combination of these peptides was tested on a panel of 128 sera from chronic active HCV carriers. Hundred and twenty six of these sera tested positive on recombinant E2s protein. Of these 126 sera, 33 sera showed at least two times higher OD values with the peptide mixture as compared to the recombinant E2 protein, 64 sera showed a similar reactivity, 16 sera showed reactivities which were 2- to 4-fold higher with the recombinant protein than with the peptide mixture, and 13 sera only reacted with the recombinant protein.

In summary, almost 90% of the sera containing antibodies against recombinant E2 protein could be detected using the above peptide mixture. For 26% of the sera, detection was even better using the peptides of the invention, than using recombinant E2 protein. A sum of OD values of >5, ie exhibited by peptides HVR I, HVR I/C1, C1a, C1b, C4a, C4b, C4c, and C4b-c (FIG. 4) is therefore considered a surprisingly high value for the serodiagnosis of antibodies directed against the E2 protein of HCV. From the experiment described above, it is also clear that a combination of recombinant E2 with the peptides of the invention is a particularly useful composition. Given the variability of the E2 protein in different HCV genotypes, the addition of genotype-specific peptides to recombinant E2 proteins may be a desired way of improving sensitivity of E2 antibody assays. For example, a variant of peptide C1a based on a reported HCV type 2a sequence HC-J6 could be LINTNG-SWHINRTALNCNDSLHTGFLASLFYTHSF (SEQ ID NO:40), and similar useful variants e.g. based on a genotype 3a sequence, could be synthesized and tested for reactivity. It should be noted that the HCV E2 protein may contain insertions or deletions in any given HCV genotype. For example, while subtype 1a and 1b sequences show contiguous sequences which can be aligned without having to insert gaps, HCV type 2a isolates encode E2 proteins which are 4 aa's longer as compared t type 1 sequences. For example, 2 additional amino acids are inserted in HCV type 2a and 2b sequences around hypervariable region II (HVR II). Therefore, a potentially useful variant of peptide HVRII, based on the HC-J6 prototype 2a sequence, would be RSIEAFRVGWGALQYEDNVTNPEDMRPYCW (SEQ ID NO:41), which is a 30-mer peptide while the subtype 1 b sequence based peptide depicted in Table 1 (SEQ ID NO:20) is only 28 aa's long. The two glutamates (symbol E) which are inserted in the subtype 2a sequence are shown underlined. Similar peptides can be easily constructed based on sequences and alignments previously published (e.g. Maertens and Stuyver, 1997).

LIST OF REFERENCES

Atherton, Shepard (1989) Solid phase peptide synthesis. IRL Press, Oxford.

Chien D, Choo Q-L, Ralston R, Spaete R, Tong M, Houghton M, Kuo G. Persistence of HCV despite antibodies to both putative envelope proteins. *The Lancet* 1993; 342: 933.

Current protocols in immunology. Eds Coligan J., Kruisbeek A., Margulis D., Shevach E. And Strober W. Wiley-Interscience, 1992.

Houbenweyl (1974) Methode der organischen chemie, vol. 15, I & II (ed. Wunch E). Thieme, Stuttgart.

Hsu H, Donets M, Greenberg H., et al. Characterization of hepatitis C virus structural proteins with a recombinant baculovirus expression system. *Hepatology* 1993; 17: 763–71.

Inoue Y, Suzuki R, Matsuura Y, et al. Expression of the amino-terminal helf of the NS1 region of the hepatitis C virus genome and detection of an antibody to the expressed protein in patients with liver diseases. *J. Gen. Virol.* 1992; 73: 2151–4.

Kohara M, Tsukiyama-Kohara K, Maki N, et al. Expression and characterization of glycoprotein gp35 of hepatitis C virus using recombinant vaccinia virus. *J. Gen. Virol.* 1992; 73: 2313–8.

Ling P D, Warren M K, Vogen S N. et al. *J. Immunol.* 1985; 135: 1857–63.

Linnen J, Wages J Jr, Zhang-Keck Z, Fry K, Krawczynski K, Alter H, Koonin E, et al. Molecular cloning and disease association of hepatitis G virus: a transfusion-transmissible agent. *Science* 1996; 271: 505–8.

Maertens, G. and Stuyver, L. (1997) Genotypes and Genetic variation of hepatitis C virus. In: Molecular Medicine of Hepatitis (Eds. Zuckerman, A. and Harrison, T.), Molecular Medical Science Series (Eds. James, K. and Morris A) John Wiley and Sons Ltd., Chichester, England, Chapter 13, pp183–233.

Major M. E. and Feinstone S. M. The molecular virology of hepatitis C. Hepatology 1997: 25: 1527–1538.

Maniatis T, Fritsch E, Sambrook J (1982) Molecular cloning: a laboratory manual. Cold Spring Harbor Laboratory Press, Cold Spring Harbor, N.Y.

Mita E, Hayashi N, Ueda K, et al. Expression of MBP-HCV NS1/F2 fusion protein in *E coli* and detection of anti-NS1/E2 antibody in type C chronic liver disease. *Biochem. Biophys. Res. Comm.* 1992; 183: 925–30.

Sambrook J, Fritsch E, Maniatis T (1989) Molecular cloning: a laboratory manual. Cold Spring Harbor Laboratory Press, Cold Spring Harbor, N.Y.

Simons J N, Pilot-Matias T J, Leary T P, Dawson G J, Desai S M, Schlauder G G, Muerhoff A S, et al. Identification of two flavivirus-like genomes in the GB hepatitis agent. *Proc Natl Acad Sci USA* 1996; 92: 3401–5.

Wengler G. (1991) Family Flaviviridae. In: 'Classification and Nomenclature of viruses, fifth report of the international committee on Taxonomy and nomenclature of viruses (Eds. Francki R, Fauquet C, Knudson D., and Brown F.) Archives of Virology, Supplementum 2, pp 223–233, Springer-Verlag, Wien, N.Y.

Yokosuka O, Ito Y, Imazeki F, Ohto M, Omata M. Detection of antibody to hepatitis C E2/NS1 protein in patients with type C hepatitis. *Bioch Biophys Res Commun* 1992; 189: 565–71.

TABLE 1

| PROTEIN | GENO TYPE | PEPTIDE | AMINO ACID SEQUENCE | POSITION | SEQ ID NUMBER |
|---|---|---|---|---|---|
| E1 | 1a | V1V2T1a | YQVRNSTGLYHVTNDCPNSSIVYEAADAILHTPGC | 192–226 | Seq ID 1 |
| | 1b | V1V2T1b | YEVRNVSGIYHVTNDCSNSSIVYEAADMIMHTPGC | 192–226 | Seq ID 2 |
| | 2c | V1V2T2c | VEVKNNSNSYMATNDCSNSSIIWQLEGAVLHTPGC | 192–226 | Seq ID 3 |
| | 2c | V1V2T2c | VEVKNTSTSYMVTNDCSNSSIVWQLEGAVLHTPGC | 192–226 | Seq ID 4 |
| | 3a | V1V2T3a | LEWRNTSGLYVLTNDCSNSSIVYEADDVILHTPGC | 192–226 | Seq ID 5 |
| | 3a | V2T3a | LTNDCSNSSIVYEADDVILHTPGC | 203–226 | Seq ID 6 |
| | 4c/4k | V1V2T4a | INYRNVSGIYHVTNDCPNSSIVYEADHHILHLPGC | 192–226 | Seq ID 7 |
| | 5a | V1V2T5a | VPYRNASGIYHITNDCPNSSIVYEADNLILHAPGC | 192–226 | Seq ID 8 |
| | 6a | V1V2T6a | LTYGNSSGLYHLTNDCSNSSIVLEADAMILHLPGC | 192–226 | Seq ID 9 |
| | 1b | V2V3 | IVYEAADMIMHTPGCVPCVRENNSSRCWV | 212–240 | Seq ID 10 |
| | 1b | V3V4 | VRENNSSRCWVALTPTLAARNASVPTTTIRRHVD | 230–263 | Seq ID 11 |
| | 1b | PC-V3V4 | PCVRENNSSRCWVALTPTLAARNASVPTTTIRRHVD | 228–263 | Seq ID 12 |
| | 1b | HR | HVDLLVGAAAFCSAMYVGDLCGSVFLVSQL | 260–290 | Seq ID 13 |
| | 1b | V5C4 | SQLFTISPRRHETVQDCNCSIYPGHITGHRMAWDMMMNWS | 288–327 | Seq ID 14 |
| | 1b | C4V6 | SIYPGHITGHRMAWDMMMNWSPTTALVVSQLLRI | 307–340 | Seq ID 15 |
| | 1b | SA | PQAVVDMVAGAHWGVLAGLAYYSMVGNWAKVLVVMLLFAGV | 341–381 | Seq ID 16 |
| | 1b | V4V5 | VALTPTLAARNASVPTTTIRRHVDSQLFTISPRRHETVQD | 240–303 | Seq ID 37 |

TABLE 1-continued

| PROTEIN | GENOTYPE | PEPTIDE | AMINO ACID SEQUENCE | POSITION | SEQ ID NUMBER |
|---|---|---|---|---|---|
| E1 (HGV) | ND | V1V2 | THACRANGQYFLTNCCAPEDIGFCLEGGCLVALGGK | ND | Seq ID 38 |
| E2 | 1b | HVR I | HTRVSGGAAASNTRGLVSLFSPGSAQKIQLVN | 384–415 | Seq ID 17 |
| | 1b | C1a | LVNTNGSWHINRTALNCNDSLQTGFFAALFYKHKF | 413–447 | Seq ID 18 |
| | 1b | C1b | NDSLQTGFFAALFYKHKFNSSGCPERLASCRSIDKFAQ | 430–467 | Seq ID 19 |
| | 1b | HVR II | RSIDKFAQGWGPLTYTEPNSSDQRPYCW | 460–487 | Seq ID 20 |
| | 1b | C2a | SDQRPYCWHYAPRPCGIVPASQVCGPVYCFTPSP | 480–513 | Seq ID 21 |
| | 1b | C2b | SQVCGPVYCFTPSPVVVGTTDRFGVPTYNWG | 500–530 | Seq ID 22 |
| | 1b | V3C3 | GVPTYNWGANDSDVLILNNTRPPRGNWFGCTWMNGTGFTKTCGG | 523–566 | Seq ID 23 |
| | 1b | V3C3' | ANDSDVLILNNTRPPRGNWFGCTWMNGTGFTKTCGG | 531–566 | Seq ID 24 |
| | 1b | C3" | TRPPRGNWFGCTWMNGTGFTKTCGG | 542–566 | Seq ID 25 |
| | 1b | V4 | TKTCGGPPCNIGGAGNNTLTCPTDCFRKHP | 561–590 | Seq ID 26 |
| | 1b | C4 | TDCFRKHPEATYARCGSGPWLTPRCMVHYPYRLWHYPCTVNFTIF | 583–627 | Seq ID 27 |
| | 1b | C4' | ARCGSGPWLTPRCMVHYPYRLWHYPCTVNFTIF | 595–627 | Seq ID 28 |
| | 1b | C4" | LTPRCMVHYPYRLWHYPCTVNFTIF | 603–627 | Seq ID 29 |
| | 1b | C4a | TVNFTIFKVRMYVGGVEHRFEAACNWTR | 621–648 | Seq ID 30 |
| | 1b | C4b | EAACNWTRGERCDLEDRDRSELSPLLLSTTEWQ | 641–673 | Seq ID 31 |
| | 1b | C4c | QWQILPCSFTTLPALSTGLIHLHQNIVDVQYLYGVG | 671–706 | Seq ID 32 |
| | 1b | SA | GVGSAVVSLVIKWEYVLLLFLLLADARICACLWMMLLIAQAE | 704–745 | Seq ID 33 |
| | 1b | HVR I/C1 | NTRGLVSLFSPGSAQKIQLVNTNGSWHINRTALN | 395–428 | Seq ID 34 |
| | 1b | C4b-c | DRSELSPLLLSTTEWQILPCSFTTLPALSTG | 658–688 | Seq ID 35 |
| | 1b | 1350 | VGTTDRFGVPTYNWGANDSD | 516–535 | Seq ID 36 |

TABLE 2

| Sample # | HVR I | C1-a | C1-b | HVR II | C2-a | C2-b | E2-13B | C3 | C3' | C3" | V4 | C4 | C4-a | C4-b | C4-c | SA | Rec E2 |
|---|---|---|---|---|---|---|---|---|---|---|---|---|---|---|---|---|---|
| 17758 | 69 | 48 | 47 | 52 | 49 | 48 | 47 | 49 | 38 | 44 | 43 | 52 | 44 | 55 | 48 | 46 | 1355 |
| 17763 | 88 | 54 | 44 | 49 | 52 | 48 | 51 | 51 | 46 | 45 | 48 | 49 | 45 | 133 | 104 | 50 | 361 |
| 17764 | 100 | 148 | 138 | 134 | 128 | 136 | 141 | 136 | 136 | 65 | 130 | 145 | 144 | 242 | 128 | 127 | 371 |
| 17766 | 91 | 97 | 145 | 96 | 80 | 87 | 90 | 90 | 95 | 47 | 75 | 89 | 163 | 139 | 99 | 86 | 173 |
| 17771 | 307 | 79 | 54 | 65 | 51 | 50 | 65 | 68 | 50 | 45 | 60 | 65 | 59 | 96 | 132 | 58 | 393 |
| 17775 | 49 | 50 | 46 | 39 | 50 | 271 | 43 | 51 | 48 | 45 | 50 | 55 | 52 | 54 | 47 | 50 | 228 |
| 17777 | 60 | 133 | 105 | 130 | 129 | 123 | 118 | 118 | 130 | 95 | 119 | 133 | 129 | 357 | 177 | 113 | 850 |
| 17779 | 373 | 328 | 285 | 330 | 284 | 343 | 281 | 323 | 316 | 283 | 297 | 318 | 343 | 341 | 309 | 282 | 720 |
| 17785 | 81 | 80 | 73 | 71 | 76 | 66 | 81 | 70 | 74 | 70 | 69 | 79 | 79 | 87 | 119 | 73 | 146 |
| 11786 | 341 | 863 | 693 | 152 | 164 | 179 | 148 | 139 | 146 | 136 | 137 | 158 | 160 | 163 | 148 | 157 | 720 |
| 17788 | 111 | 553 | 120 | 137 | 69 | 121 | 121 | 119 | 111 | 110 | 103 | 140 | 132 | 131 | 48 | 47 | 934 |
| 17789 | 1316 | 49 | 47 | 46 | 49 | 45 | 53 | 51 | 43 | 42 | 50 | 49 | 52 | 48 | 48 | 1178 |
| 11790 | 234 | 233 | 182 | 223 | 130 | 224 | 185 | 185 | 186 | 184 | 179 | 216 | 218 | 1347 | 853 | 207 | 1534 |
| 17791 | 269 | 194 | 177 | 192 | 123 | 203 | 172 | 192 | 157 | 184 | 184 | 200 | 195 | 211 | 187 | 190 | 287 |
| 17797 | 260 | 264 | 248 | 257 | 240 | 281 | 249 | 237 | 246 | 221 | 223 | 283 | 261 | 272 | 231 | 243 | 1357 |
| 17798 | 52 | 53 | 50 | 47 | 52 | 54 | 50 | 53 | 49 | 51 | 50 | 51 | 50 | 1036 | 51 | 51 | 1161 |
| 17799 | 225 | 89 | 81 | 86 | 85 | 100 | 76 | 85 | 87 | 82 | 84 | 86 | 92 | 115 | 86 | 76 | 362 |
| 17802 | 42 | 51 | 44 | 47 | 50 | 133 | 48 | 52 | 51 | 48 | 51 | 56 | 76 | 773 | 157 | 56 | 882 |
| 17807 | 49 | 133 | 60 | 59 | 66 | 62 | 62 | 59 | 57 | 56 | 57 | 63 | 65 | 62 | 57 | 52 | 605 |
| 17808 | 89 | 121 | 117 | 109 | 106 | 1051 | 118 | 875 | 133 | 116 | 123 | 126 | 393 | 228 | 109 | 126 | 1354 |
| 17810 | 327 | 220 | 199 | 222 | 195 | 200 | 221 | 182 | 197 | 182 | 196 | 209 | 266 | 222 | 195 | 199 | 422 |
| 17818 | 224 | 134 | 115 | 126 | 118 | 115 | 128 | 108 | 109 | 98 | 111 | 113 | 112 | 117 | 109 | 108 | 230 |
| 17821 | 671 | 243 | 214 | 282 | 238 | 232 | 228 | 217 | 234 | 197 | 216 | 222 | 218 | 557 | 810 | 205 | 1046 |
| 17825 | 397 | 320 | 264 | 284 | 282 | 286 | 289 | 277 | 276 | 274 | 276 | 306 | 273 | 391 | 399 | 277 | 514 |
| 17826 | 92 | 109 | 111 | 99 | 114 | 126 | 113 | 98 | 104 | 84 | 105 | 121 | 122 | 126 | 145 | 113 | 695 |
| 17827 | 45 | 47 | 46 | 47 | 48 | 49 | 48 | 49 | 49 | 47 | 49 | 50 | 50 | 261 | 113 | 47 | 320 |
| 17832 | 151 | 65 | 55 | 70 | 78 | 63 | 77 | 72 | 68 | 59 | 64 | 70 | 62 | 54 | 57 | 49 | 288 |
| 17838 | 212 | 167 | 166 | 164 | 156 | 165 | 164 | 146 | 160 | 154 | 150 | 165 | 165 | 161 | 272 | 157 | 305 |
| 17839 | 48 | 94 | 117 | 61 | 61 | 51 | 58 | 51 | 46 | 52 | 58 | 55 | 87 | 60 | 95 | 66 | 182 |
| 17840 | 318 | 323 | 347 | 317 | 329 | 338 | 320 | 305 | 326 | 302 | 312 | 343 | 355 | 322 | 318 | 337 | 417 |
| 17842 | 161 | 174 | 185 | 176 | 168 | 163 | 159 | 157 | 163 | 156 | 150 | 168 | 151 | 154 | 138 | 153 | 195 |
| 17844 | 122 | 94 | 90 | 88 | 98 | 78 | 92 | 88 | 84 | 77 | 85 | 94 | 61 | 214 | 51 | 73 | 166 |
| 17849 | 1469 | 68 | 75 | 49 | 54 | 629 | 52 | 53 | 46 | 46 | 51 | 54 | 119 | 1102 | 55 | 47 | 1393 |
| 17870 | 125 | 236 | 148 | 114 | 128 | 133 | 135 | 116 | 132 | 109 | 135 | 151 | 118 | 293 | 120 | 45 | 197 |
| 17879 | 209 | 195 | 201 | 222 | 195 | 215 | 225 | 191 | 194 | 181 | 218 | 209 | 209 | 255 | 253 | 199 | 325 |
| 17983 | 438 | 54 | 50 | 48 | 52 | 46 | 50 | 54 | 46 | 46 | 51 | 52 | 46 | 55 | 53 | 48 | 216 |
| 17999 | 276 | 201 | 200 | 202 | 190 | 187 | 191 | 169 | 176 | 150 | 190 | 205 | 186 | 321 | 535 | 198 | 697 |
| 8242 | 162 | 114 | 114 | 127 | 140 | 114 | 120 | 117 | 103 | 120 | 117 | 107 | 112 | 161 | 152 | 128 | 340 |
| 8243 | 188 | 191 | 171 | 175 | 204 | 172 | 189 | 174 | 186 | 174 | 176 | 205 | 200 | 206 | 177 | 178 | 225 |
| 8247 | 248 | 169 | 137 | 127 | 120 | 110 | 122 | 96 | 111 | 104 | 114 | 128 | 104 | 130 | 150 | 118 | 215 |
| 8250 | 129 | 161 | 127 | 150 | 164 | 144 | 154 | 125 | 134 | 122 | 142 | 151 | 125 | 146 | 137 | 140 | 165 |
| 8317 | 112 | 131 | 115 | 123 | 113 | 111 | 144 | 95 | 103 | 95 | 108 | 118 | 108 | 158 | 126 | 111 | 198 |
| 8320 | 463 | 433 | 337 | 473 | 435 | 445 | 363 | 345 | 503 | 384 | 362 | 369 | 405 | 446 | 432 | 378 | 474 |
| 8329 | 119 | 126 | 123 | 160 | 143 | 145 | 142 | 117 | 135 | 121 | 122 | 126 | 131 | 152 | 148 | 132 | 163 |
| 8330 | 198 | 271 | 210 | 210 | 207 | 196 | 216 | 178 | 194 | 206 | 209 | 215 | 186 | 356 | 45 | 51 | 536 |
| 8332 | 154 | 141 | 128 | 141 | 132 | 116 | 129 | 110 | 123 | 112 | 135 | 140 | 123 | 147 | 312 | 144 | 290 |

TABLE 2-continued

| Sample # | HVR I | C1-a | C1-b | HVR II | C2-a | C2-b | E2-13 B | C3 | C3' | C3" | V4 | C4 | C4-a | C4-b | C4-c | SA | Rec E2 |
|---|---|---|---|---|---|---|---|---|---|---|---|---|---|---|---|---|---|
| 8333 | 57 | 67 | 50 | 51 | 52 | 52 | 50 | 54 | 50 | 50 | 50 | 56 | 48 | 480 | 65 | 52 | 1108 |
| 8334 | 283 | 66 | 64 | 80 | 68 | 69 | 84 | 79 | 65 | 52 | 67 | 74 | 72 | 180 | 191 | 90 | 348 |
| 8337 | 162 | 105 | 99 | 108 | 103 | 92 | 104 | 86 | 93 | 80 | 101 | 107 | 108 | 124 | 118 | 110 | 142 |
| 8339 | 50 | 49 | 52 | 62 | 54 | 46 | 54 | 51 | 47 | 41 | 51 | 55 | 53 | 413 | 49 | 50 | 247 |
| 8344 | 59 | 52 | 50 | 51 | 58 | 48 | 54 | 52 | 47 | 48 | 55 | 53 | 58 | 63 | 63 | 60 | 59 |
| 8351 | 163 | 114 | 105 | 111 | 101 | 91 | 98 | 97 | 92 | 78 | 110 | 111 | 115 | 141 | 179 | 112 | 154 |
| 8362 | 211 | 54 | 50 | 47 | 55 | 119 | 53 | 53 | 44 | 45 | 51 | 54 | 59 | 60 | 58 | 55 | 165 |
| 8364 | 110 | 308 | 106 | 112 | 112 | 107 | 98 | 102 | 108 | 92 | 116 | 152 | 133 | 208 | 169 | 132 | 671 |
| 8365 | 69 | 84 | 94 | 67 | 77 | 74 | 55 | 73 | 70 | 69 | 70 | 79 | 73 | 69 | 88 | 66 | 86 |
| 8367 | 218 | 189 | 171 | 201 | 204 | 174 | 191 | 156 | 158 | 140 | 183 | 186 | 294 | 197 | 186 | 171 | 303 |
| 8374 | 575 | 113 | 95 | 114 | 110 | 93 | 100 | 92 | 106 | 88 | 103 | 125 | 118 | 112 | 111 | 106 | 143 |
| 8377 | 364 | 232 | 229 | 225 | 211 | 202 | 233 | 189 | 207 | 170 | 209 | 205 | 230 | 234 | 218 | 221 | 293 |
| 8382 | 314 | 211 | 187 | 196 | 207 | 173 | 208 | 181 | 158 | 150 | 181 | 187 | 201 | 223 | 189 | 211 | 265 |
| 8383 | 51 | 100 | 102 | 55 | 58 | 48 | 57 | 53 | 53 | 50 | 52 | 57 | 66 | 94 | 63 | 56 | 285 |
| V1200 | 52 | 55 | 52 | 56 | 55 | 53 | 50 | 54 | 50 | 52 | 51 | 50 | 50 | 52 | 53 | 54 | 50 |
| V1201 | 118 | 147 | 138 | 136 | 224 | 144 | 123 | 137 | 140 | 111 | 135 | 154 | 166 | 171 | 137 | 155 | 162 |
| V1202 | 274 | 308 | 284 | 170 | 290 | 286 | 282 | 248 | 277 | 229 | 271 | 306 | 287 | 330 | 268 | 295 | 329 |
| V1204 | 130 | 134 | 135 | 127 | 141 | 128 | 79 | 113 | 119 | 106 | 131 | 144 | 145 | 144 | 130 | 144 | 159 |

TABLE 3

| | E1 antigens | | | | | | |
|---|---|---|---|---|---|---|---|
| Sample # | No peptide | V1V2 | V2V3 | V3V4 | HR/SA | V5 | C4V6 | rec E1s |
| No sample | 0.011 | 0.007 | 0.011 | 0.014 | 0.009 | 0.007 | 0.009 | 0.056 |
| 30108 | 0.03 | 0.035 | 0.04 | 0.034 | 0.032 | 0.03 | 0.234 | 0.378 |
| 30109 | 0.032 | 0.033 | 0.035 | 0.028 | 0.024 | 0.026 | 0.227 | 0.368 |
| 30110 | 0.021 | 0.545 | 0.02 | 0.019 | 0.016 | 0.017 | 0.047 | 0.669 |
| 30111 | 0.017 | 0.614 | 0.019 | 0.018 | 0.017 | 0.015 | 0.064 | 0.796 |
| 30112 | 0.037 | 0.069 | 0.035 | 0.034 | 0.031 | 0.031 | 0.048 | 0.187 |
| 30113 | 0.042 | 0.083 | 0.136 | 0.039 | 0.034 | 0.035 | 0.063 | 0.226 |
| 30114 | 0.042 | 0.099 | 0.036 | 0.035 | 0.035 | 0.037 | 0.058 | 0.267 |
| 30115 | 0.021 | 0.114 | 0.023 | 0.021 | 0.02 | 0.02 | 0.189 | 0.339 |
| 30116 | 0.019 | 0.442 | 0.025 | 0.022 | 0.022 | 0.018 | 0.056 | 0.645 |
| 30117 | 0.027 | 0.062 | 0.047 | 0.043 | 0.041 | 0.038 | 0.066 | 0.164 |
| 30118 | 0.122 | 0.216 | 0.126 | 0.12 | 0.11 | 0.125 | 0.696 | 0.923 |
| 30119 | 0.023 | 0.028 | 0.031 | 0.028 | 0.023 | 0.024 | 0.23 | 0.426 |
| 30120 | 0.025 | 0.024 | 0.027 | 0.025 | 0.039 | 0.027 | 0.03 | 0.024 |
| 30121 | 0.03 | 0.033 | 0.033 | 0.029 | 0.052 | 0.034 | 0.037 | 0.032 |
| 30122 | 0.029 | 0.031 | 0.056 | 0.03 | 0.052 | 0.033 | 0.035 | 0.03 |
| 30123 | 0.085 | 0.081 | 0.076 | 0.075 | 0.087 | 0.071 | 0.094 | 0.137 |
| 30124 | 0.022 | 0.084 | 0.022 | 0.022 | 0.023 | 0.022 | 0.193 | 0.391 |
| 30125 | 0.095 | 0.128 | 0.091 | 0.089 | 0.172 | 0.159 | 0.47 | 0.708 |
| 17805 | 0.038 | 0.051 | 0.039 | 0.033 | 0.09 | 0.154 | 0.738 | 1.169 |
| 13059 | 0.011 | 0.011 | 0.012 | 0.012 | 0.014 | 0.012 | 0.229 | 0.681 |
| Chimp1 | 0.095 | 0.38 | 0.276 | 0.126 | 0.098 | 0.095 | 0.099 | 0.805 |
| Chimp2 | 0.026 | 0.234 | 0.143 | 0.035 | 0.036 | 0.038 | 0.354 | 0.822 |
| Chimp3 | 0.018 | 0.017 | 0.02 | 0.022 | 0.023 | 0.019 | 0.141 | 0.353 |

TABLE 4

| | E2 antigens | | | | | | | | | | | | | | | |
|---|---|---|---|---|---|---|---|---|---|---|---|---|---|---|---|---|
| Sample | peptide | HVR I | C1-a | C1-b | HVR II | C2-a | C2-b | C3 | C3' | C3" | V4 | C4 | C4-a | C4-b | C4-c | recE2h |
| No sample | 0.006 | 0.009 | 0.011 | 0.015 | 0.007 | 0.006 | 0.01 | 0.01 | 0.01 | 0.01 | 0.01 | 0.01 | 0.007 | 0.007 | 0.009 | 0.032 |
| 30108 | 0.036 | 0.747 | 0.848 | 0.969 | 0.032 | 0.033 | 0.03 | 0.04 | 0.02 | 0.02 | 0.03 | 0.03 | 0.041 | 0.026 | 0.031 | 0.988 |
| 30109 | 0.027 | 0.849 | 0.93 | 1.053 | 0.027 | 0.032 | 0.03 | 0.03 | 0.02 | 0.03 | 0.03 | 0.02 | 0.038 | 0.023 | 0.026 | 1.079 |
| 30110 | 0.018 | 0.026 | 0.021 | 0.044 | 0.019 | 0.024 | 0.02 | 0.02 | 0.02 | 0.02 | 0.02 | 0.03 | 0.023 | 0.026 | 0.056 | 0.11 |
| 30111 | 0.017 | 0.02 | 0.021 | 0.088 | 0.018 | 0.02 | 0.02 | 0.02 | 0.01 | 0.02 | 0.02 | 0.03 | 0.022 | 0.028 | 0.07 | 0.137 |
| 30112 | 0.037 | 0.092 | 0.052 | 0.177 | 0.044 | 0.048 | 0.04 | 0.04 | 0.04 | 0.04 | 0.04 | 0.05 | 0.043 | 0.562 | 0.053 | 0.947 |
| 30113 | 0.045 | 0.104 | 0.054 | 0.276 | 0.051 | 0.047 | 0.05 | 0.03 | 0.04 | 0.04 | 0.04 | 0.05 | 0.054 | 0.633 | 0.07 | 1.003 |
| 30114 | 0.045 | 0.112 | 0.075 | 0.726 | 0.046 | 0.041 | 0.05 | 0.05 | 0.03 | 0.04 | 0.04 | 0.06 | 0.054 | 0.646 | 0.067 | 1.065 |
| 30115 | 0.022 | 0.982 | 0.034 | 0.064 | 0.025 | 0.025 | 0.02 | 0.03 | 0.02 | 0.03 | 0.03 | 0.02 | 0.03 | 0.097 | 0.031 | 0.413 |
| 30116 | 0.015 | 0.023 | 0.02 | 0.04 | 0.017 | 0.02 | 0.02 | 0.02 | 0.02 | 0.02 | 0.02 | 0.03 | 0.023 | 0.022 | 0.046 | 0.084 |
| 30117 | 0.04 | 0.087 | 0.048 | 0.119 | 0.037 | 0.044 | 0.05 | 0.05 | 0.05 | 0.04 | 0.04 | 0.04 | 0.041 | 0.547 | 0.049 | 0.935 |
| 30118 | 0.112 | 0.213 | 0.122 | 0.119 | 0.119 | 0.121 | 0.12 | 0.12 | 0.11 | 0.05 | 0.11 | 0.1 | 0.117 | 0.105 | 0.2 | 0.289 |
| 30119 | 0.03 | 0.954 | 1.012 | 1.128 | 0.026 | 0.029 | 0.03 | 0.03 | 0.02 | 0.02 | 0.03 | 0.03 | 0.035 | 0.026 | 0.03 | 1.123 |
| 30120 | 0.031 | 0.427 | 0.208 | 0.208 | 0.03 | 0.033 | 0.03 | 0.04 | 0.03 | 0.03 | 0.03 | 0.03 | 0.033 | 0.032 | 0.032 | 0.577 |
| 30121 | 0.033 | 0.734 | 0.463 | 0.398 | 0.037 | 0.042 | 0.04 | 0.05 | 0.04 | 0.03 | 0.04 | 0.03 | 0.04 | 0.034 | 0.037 | 0.963 |

TABLE 4-continued

| Sample | peptide | E2 antigens | | | | | | | | | | | | | | |
|---|---|---|---|---|---|---|---|---|---|---|---|---|---|---|---|---|
| | | HVR I | C1-a | C1-b | HVR II | C2-a | C2-b | C3 | C3' | C3" | V4 | C4 | C4-a | C4-b | C4-c | recE2h |
| 30122 | 0.03 | 0.661 | 0.413 | 0.365 | 0.043 | 0.034 | 0.03 | 0.04 | 0.04 | 0.03 | 0.03 | 0.03 | 0.038 | 0.03 | 0.034 | 0.907 |
| 30123 | 0.079 | 0.11 | 0.576 | 0.789 | 0.09 | 0.108 | 0.09 | 0.08 | 0.08 | 0.06 | 0.07 | 0.06 | 0.091 | 0.078 | 0.077 | 0.916 |
| 30124 | 0.02 | 0.939 | 0.041 | 0.065 | 0.028 | 0.237 | 0.04 | 0.04 | 0.02 | 0.03 | 0.02 | 0.02 | 0.038 | 0.108 | 0.049 | 0.4 |
| 30125 | 0.096 | 0.133 | 0.103 | 0.096 | 0.097 | 0.115 | 0.15 | 0.14 | 0.09 | 0.09 | 0.09 | 0.1 | 0.1 | 0.092 | 0.183 | 0.227 |
| 17805 | 0.042 | 0.255 | 0.074 | 0.078 | 0.071 | 0.045 | 0.06 | 0.06 | 0.05 | 0.04 | 0.06 | 0.04 | 0.163 | 0.043 | 0.831 | 0.881 |
| 13059 | 0.013 | 0.47 | 0.02 | 0.019 | 0.018 | 0.022 | 0.02 | 0.03 | 0.02 | 0.01 | 0.01 | 0.02 | 0.36 | 0.052 | 0.904 | 0.944 |
| Chimp1 | 0.102 | 0.103 | 0.116 | 0.118 | 0.23 | 0.109 | 0.12 | 0.19 | 0.17 | 0.19 | 0.1 | 0.1 | 0.087 | 0.098 | 0.095 | 0.581 |
| Chimp2 | 0.028 | 0.181 | 0.261 | 0.261 | 0.056 | 0.032 | 0.03 | 0.04 | 0.04 | 0.04 | 0.04 | 0.04 | 0.188 | 0.035 | 0.033 | 1.008 |
| Chimp3 | 0.058 | 0.035 | 0.162 | 0.086 | 0.026 | 0.062 | 0.02 | 0.03 | 0.04 | 0.02 | 0.03 | 0.03 | 0.023 | 0.02 | 0.026 | 1.327 |

TABLE 5

| Sample | HCV PCR | Genotype | E1 peptides | | | | | | | |
|---|---|---|---|---|---|---|---|---|---|---|
| | | | V1V2 | V2V3 | V3V4 | V4V5 | HR/SA | V5C4 | C4V5 | E1s |
| Patient 1 | | | | | | | | | | |
| 14/8/90 | pos | 3a | 0.014 | 0.03 | 0.06 | 0.034 | 0.037 | 0.048 | 0.045 | 0.051 |
| 01/06/91 | | | 0.03 | 0.032 | 0.064 | 0.041 | 0.041 | 0.051 | 0.048 | 0.045 |
| 20/9/91 | neg | | 0.06 | 0.064 | 0.064 | 0.037 | 0.039 | 0.05 | 0.398 | 0.045 |
| 13/3/92 | | | 0.034 | 0.041 | 0.037 | 0.034 | 0.037 | 0.046 | 0.044 | 0.04 |
| 04/09/92 | neg | | 0.037 | 0.041 | 0.039 | 0.037 | 0.037 | 0.052 | 0.048 | 0.043 |
| 24/9/93 | | | 0.048 | 0.051 | 0.05 | 0.046 | 0.052 | 0.048 | 0.047 | 0.042 |
| 20/10/94 | neg | | 0.045 | 0.048 | 0.398 | 0.044 | 0.048 | 0.047 | 0.045 | 0.041 |
| 23/10/95 | | | 0.051 | 0.045 | 0.045 | 0.04 | 0.043 | 0.042 | 0.041 | 0.051 |
| 10/12/96 | pos? | | 0.037 | 0.041 | 0.033 | 0.034 | 0.035 | 0.039 | 0.038 | 0.045 |
| Patient 2 | | | | | | | | | | |
| 15/2/90 | | | 0.106 | 0.103 | 0.104 | 0.108 | 0.104 | 0.949 | 0.872 | 1.03 |
| 03/05/90 | pos | 1a | 0.103 | 0.109 | 0.106 | 0.104 | 0.108 | 0.828 | 0.859 | 1.04 |
| 04/12/90 | | | 0.096 | 0.103 | 0.105 | 0.103 | 0.095 | 0.737 | 0.848 | 1.218 |
| 23/9/91 | | | 0.063 | 0.078 | 0.078 | 0.067 | 0.072 | 0.318 | 0.354 | 0.66 |
| 14/4/92 | | | 0.099 | 0.106 | 0.099 | 0.1 | 0.096 | 0.219 | 0.255 | 0.491 |
| 18/12/92 | | | 0.104 | 0.106 | 0.102 | 0.105 | 0.101 | 0.222 | 0.249 | 0.448 |
| 26/3/93 | | | 0.089 | 0.095 | 0.09 | 0.085 | 0.082 | 0.168 | 0.194 | 0.357 |
| 30/9/93 | neg | | 0.092 | 0.081 | 0.089 | 0.09 | 0.088 | 0.17 | 0.18 | 0.35 |
| 17/6/94 | pos | 1a | 0.084 | 0.09 | 0.096 | 0.599 | 0.095 | 0.154 | 0.166 | 0.32 |
| 18/12/95 | | | 0.072 | 0.077 | 0.077 | 0.077 | 0.081 | 0.111 | 0.121 | 0.206 |
| 23/12/96 | neg | | 0.065 | 0.078 | 0.074 | 0.073 | 0.078 | 0.106 | 0.108 | 0.199 |
| Patient 3 | | | | | | | | | | |
| 15/04/93 | | | 0.005 | 0.006 | 0.005 | 0.004 | 0.006 | 0.005 | 0.006 | 0.007 |
| 06/09/94 | pos | 3a | 0.007 | 0.008 | 0.007 | 0.008 | 0.007 | 0.006 | 0.006 | 0.009 |
| 30/10/95 | neg | | 0.007 | 0.01 | 0.009 | 0.009 | 0.009 | 0.008 | 0.007 | 0.011 |
| 18/11/96 | pos? | 1b | 0.012 | 0.012 | 0.012 | 0.011 | 0.01 | 0.009 | 0.009 | 0.012 |
| Patient 4 | | | | | | | | | | |
| 12/04/91 | pos | 1a | 0.006 | 0.007 | 0.006 | 0.006 | 0.007 | 0.006 | 0.006 | 0.01 |
| 23/09/91 | neg | | 0.01 | 0.01 | 0.008 | 0.009 | 0.009 | 0.006 | 0.008 | 0.013 |
| 27/07/92 | neg | | 0.007 | 0.009 | 0.007 | 0.008 | 0.007 | 0.006 | 0.007 | 0.01 |
| 11/06/93 | neg | | 0.009 | 0.011 | 0.009 | 0.01 | 0.009 | 0.007 | 0.006 | 0.011 |
| 29/11/96 | pos | 1a | 0.007 | 0.01 | 0.008 | 0.007 | 0.007 | 0.005 | 0.006 | 0.008 |
| Patient 5 | | | | | | | | | | |
| 18/09/92 | pos | | 0.017 | 0.01 | 0.008 | 0.007 | 0.008 | 0.178 | 0.196 | 0.537 |
| 17/12/93 | neg | | 0.012 | 0.014 | 0.011 | 0.01 | 0.011 | 0.039 | 0.04 | 0.231 |
| 15/11/96 | neg | | 0.012 | 0.014 | 0.012 | 0.01 | 0.01 | 0.026 | 0.017 | 0.116 |
| Patient 6 | | | | | | | | | | |
| 10/05/90 | pos | | 0.311 | 0.006 | 0.007 | 0.005 | 0.006 | 0.004 | 0.01 | 0.544 |
| 11/10/91 | neg | | 0.284 | 0.007 | 0.007 | 0.006 | 0.007 | 0.006 | 0.013 | 0.605 |
| Patient 7 | | | | | | | | | | |
| 10/10/91 | pos | 1b | 0.009 | 0.01 | 0.009 | 0.008 | 0.008 | 0.008 | 0.01 | 0.043 |
| 18/12/92 | neg | | 0.01 | 0.011 | 0.011 | 0.009 | 0.009 | 0.008 | 0.011 | 0.043 |
| 28/06/93 | neg | | 0.006 | 0.006 | 0.007 | 0.006 | 0.007 | 0.005 | 0.008 | 0.021 |
| 10/03/97 | pos | 1b | 0.008 | 0.008 | 0.007 | 0.008 | 0.007 | 0.006 | 0.008 | 0.012 |
| Patient 8 | | | | | | | | | | |
| 19/08/91 | neg | | 0.008 | 0.009 | 0.008 | 0.008 | 0.008 | 0.006 | 0.008 | 0.009 |
| 17/07/95 | pos | 1b | 0.01 | 0.009 | 0.009 | 0.009 | 0.006 | 0.007 | 0.007 | 0.018 |

TABLE 5-continued

|  | HCV | E1 peptides | | | | | | | | |
|---|---|---|---|---|---|---|---|---|---|---|
| Sample | PCR | Genotype | V1V2 | V2V3 | V3V4 | V4V5 | HR/SA | V5C4 | C4V5 | E1s |
| 09/10/95 | pos | 1b | 0.007 | 0.007 | 0.008 | 0.005 | 0.006 | 0.007 | 0.007 | 0.009 |
| 15/12/95 | neg |  | 0.008 | 0.009 | 0.008 | 0.009 | 0.008 | 0.007 | 0.007 | 0.011 |
| 04/03/96 | neg |  | 0.009 | 0.011 | 0.01 | 0.011 | 0.009 | 0.008 | 0.007 | 0.01 |
| 02/09/96 | neg |  | 0.01 | 0.011 | 0.011 | 0.01 | 0.01 | 0.008 | 0.008 | 0.013 |
| Patient 9 | | | | | | | | | | |
| 26/08/91 | pos | 1b/2ac | 0.044 | 0.015 | 0.022 | 0.023 | 0.028 | 0.031 | 0.034 | 0.115 |
| 21/12/93 | neg |  | 0.033 | 0.017 | 0.021 | 0.027 | 0.022 | 0.025 | 0.023 | 0.048 |
| 20/12/94 | pos | 1b | 0.023 | 0.016 | 0.015 | 0.028 | 0.019 | 0.028 | 0.034 | 0.077 |
| 21/12/95 | pos | 1b | 0.019 | 0.029 | 0.024 | 0.027 | 0.027 | 0.031 | 0.034 | 0.048 |
| Patient 10 | | | | | | | | | | |
| 27/04/92 | pos | 1b | 0.128 | 0.024 | 0.02 | 0.023 | 0.026 | 0.118 | 0.449 | 0.68 |
| 01/06/93 | neg |  | 0.107 | 0.03 | 0.029 | 0.027 | 0.026 | 0.098 | 0.385 | 0.667 |
| Patient 11 | | | | | | | | | | |
| 09/11/90 | neg |  | 0.018 | 0.019 | 0.012 | 0.013 | 0.015 | 0.087 | 0.141 | 0.591 |
| 12/07/91 | pos | 1b | 0.023 | 0.023 | 0.016 | 0.02 | 0.018 | 0.073 | 0.1 | 0.466 |
| 28/05/93 | pos |  | 0.008 | 0.009 | 0.009 | 0.005 | 0.008 | 0.123 | 0.173 | 0.495 |
| 20/01/95 | neg |  | 0.011 | 0.009 | 0.008 | 0.007 | 0.007 | 0.026 | 0.047 | 0.187 |
| 08/01/96 | neg |  | 0.012 | 0.013 | 0.01 | 0.009 | 0.009 | 0.025 | 0.031 | 0.21 |
| 07/02/97 | neg |  | 0.019 | 0.019 | 0.014 | 0.014 | 0.013 | 0.027 | 0.051 | 0.203 |
| Patient 12 | | | | | | | | | | |
| 11/05/92 | pos | 1b | 0.017 | 0.013 | 0.011 | 0.014 | 0.015 | 0.227 | 0.173 | 0.425 |
| 26/02/93 | neg |  | 0.022 | 0.014 | 0.013 | 0.013 | 0.014 | 0.178 | 0.264 | 0.417 |
| 12/08/93 | pos | 1b | 0.016 | 0.016 | 0.016 | 0.014 | 0.015 | 0.29 | 0.387 | 0.63 |
| Patient 13 | | | | | | | | | | |
| 07/01/91 | pos | 1b | 0.027 | 0.017 | 0.021 | 0.026 | 0.026 | 0.04 | 0.074 | 0.062 |
| 19/08/91 | neg |  | 0.018 | 0.018 | 0.015 | 0.013 | 0.012 | 0.021 | 0.009 | 0.043 |
| 21/08/92 | pos |  | 0.015 | 0.012 | 0.015 | 0.014 | 0.017 | 0.015 | 0.021 | 0.023 |
| 06/08/93 | neg |  | 0.019 | 0.018 | 0.016 | 0.021 | 0.016 | 0.01 | 0.011 | 0.02 |
| 06/03/95 | pos | 1b | 0.027 | 0.026 | 0.018 | 0.015 | 0.018 | 0.02 | 0.023 | 0.028 |
| 12/04/96 | neg |  | 0.03 | 0.017 | 0.018 | 0.036 | 0.021 | 0.027 | 0.027 | 0.022 |
| Patient 14 | | | | | | | | | | |
| 22/11/94 | pos | 1b | 0.016 | 0.011 | 0.013 | 0.013 | 0.026 | 0.318 | 0.437 | 0.461 |
| 11/10/95 | pos |  | 0.024 | 0.014 | 0.014 | 0.018 | 0.019 | 0.039 | 0.061 | 0.059 |
| 15/02/96 | neg |  | 0.032 | 0.022 | 0.021 | 0.023 | 0.016 | 0.031 | 0.041 | 0.102 |
| Patient 15 | | | | | | | | | | |
| 04/12/90 | pos | 1b | 0.003 | 0.005 | 0.005 | 0.004 | 0.005 | 0.005 | 0.005 | 0.019 |
| 29/11/90 | neg |  | 0.005 | 0.005 | 0.005 | 0.006 | 0.005 | 0.008 | 0.006 | 0.011 |
| 09/10/92 | pos | 1b | 0.006 | 0.008 | 0.007 | 0.007 | 0.007 | 0.006 | 0.005 | 0.012 |
| 25/03/96 | neg |  | 0.006 | 0.008 | 0.007 | 0.006 | 0.006 | 0.004 | 0.007 | 0.012 |
| Patient 16 | | | | | | | | | | |
| 16/12/91 | pos | 3a | 0.003 | 0.004 | 0.006 | 0.004 | 0.004 | 0.08 | 0.102 | 0.435 |
| 04/10/93 | neg |  | 0.006 | 0.007 | 0.007 | 0.006 | 0.008 | 0.028 | 0.033 | 0.253 |
| 12/09/94 | neg |  | 0.004 | 0.008 | 0.006 | 0.005 | 0.005 | 0.034 | 0.038 | 0.197 |
| 09/09/96 | neg |  | 0.004 | 0.008 | 0.007 | 0.006 | 0.005 | 0.008 | 0.013 | 0.08 |
| Patient 17 | | | | | | | | | | |
| 24/04/97 | pos | 1b | 0.076 | 0.006 | 0.008 | 0.004 | 0.009 | 0.203 | 0.327 | 1.196 |
| Patient 18 | | | | | | | | | | |
| 08/01/97 | neg |  | 0.006 | 0.007 | 0.007 | 0.007 | 0.006 | 0.006 | 0.008 | 0.009 |
| Blank |  |  | 0.006 | 0.009 | 0.009 | 0.006 | 0.006 | 0.007 | 0.006 | 0.009 |

TABLE 6

| Sample # | Blank | E1 V1V2 |
|---|---|---|
| 20188 | 68 | 74 |
| 20189 | 77 | 73 |
| 20251 | 170 | 150 |
| 20252 | 490 | 1319 |
| 20253 | 92 | 70 |
| 20254 | 50 | 55 |
| 20255 | 81 | 88 |
| 20256 | 56 | 62 |
| 20266 | 119 | 134 |
| 20271 | 77 | 78 |
| 20272 | 61 | 69 |
| 21010 | 129 | 135 |
| 21011 | 159 | 161 |
| 21012 | 120 | 93 |
| 21286 | 108 | 105 |

What is claimed is:

1. An isolated HCV E2 envelope peptide as defined by any of SEQ ID NOs: 18–36.

2. An isolated HCV E2 envelope peptide consisting of up to 45 contiguous amino acids wherein an amino acid sequence selected from SEQ ID NOs: 18–36 is present in said peptide.

3. An isolated peptide selected from the group consisting of:
 a peptide of 21 to 27 contiguous amino acids of SEQ ID NO:20 or 30;
 a peptide of 21 to 29 contiguous amino acids of SEQ ID NO:26;
 a peptide of 21 to 30 contiguous amino acids of SEQ ID NO:22 or 35;
 a peptide of 21 to 31 contiguous amino acids of SEQ ID NO:17 or 34;
 a peptide of 21 to 32 contiguous amino acids of SEQ ID NO:31;
 a peptide of 21 to 33 contiguous amino acids of SEQ ID NO:21;
 a peptide of 21 to 34 contiguous amino acids of SEQ ID NO:18;
 a peptide of 21 to 35 contiguous amino acids of SEQ ID NO:32;
 a peptide of 21 to 37 contiguous amino acids of SEQ ID NO:19;
 a peptide of 21 to 41 contiguous amino acids of SEQ ID NO:33;
 a peptide of 21 to 43 contiguous amino acids of SEQ ID NO:23; and
 a peptide of 21 to 44 contiguous amino acids of SEQ ID NO:27.

4. The isolated peptide of any of claims 1, 2 and 3 which is synthesized chemically.

5. The isolated peptide of any of claims 1, 2 and 3 which is synthesized using recombinant DNA techniques.

6. The isolated peptide of claim 5 wherein said peptide is synthesized using a plasmid vector comprising a nucleotide sequence encoding said peptide operably linked to transcription regulatory elements.

7. The isolated peptide of any of claims 1, 2 and 3 which is biotinylated or which is containing cysteine bridges.

8. The isolated peptide of any of claims 1, 2 and 3 which binds and recognizes anti-HCV-related virus antibodies.

9. The isolated peptide of claim 7 which binds and recognizes anti-HCV-related virus antibodies.

10. A combination of peptides comprising a peptide of any of claims 1, 2 and 3.

11. A combination of peptides comprising a peptide of claim 7.

12. A combination of peptides comprising a peptide of claim 8.

13. A composition comprising an isolated peptide of any of claims 1, 2 and 3.

14. A composition comprising an isolated peptide of claim 7.

15. A composition comprising an isolated peptide of claim 8.

16. An assay kit for detecting the presence of anti-HCV-related virus antibodies within a sample of body fluid comprising at least one peptide of any of claims 1, 2 and 3.

17. An assay kit for detecting the presence of anti-HCV-related virus antibodies within a sample of body fluid comprising a combination of peptides of claim 7.

18. An assay kit for detecting the presence of anti-HCV-related virus antibodies within a sample of body fluid comprising a combination of peptides of claim 8.

19. An assay kit for detecting the presence of anti-HCV-related virus antibodies within a sample of body fluid comprising a combination of peptides of claim 10.

20. An assay kit for detecting the presence of anti-HCV-related virus antibodies within a sample of body fluid comprising a combination of peptides of claim 11.

21. A method of immunizing a human against infection with HCV-related virus or any mutated strain thereof, comprising administering to said human at least one peptide according to any one of claims 1, 2 and 3.

22. A method of immunizing a human against infection with HCV-related virus or any mutated strain thereof, comprising administering to said human at least one peptide according to claim 4.

23. A method of immunizing a human against infection with HCV-related virus or any mutated strain thereof, comprising administering to said human at least one peptide according to claim 5.

24. A method of immunizing a human against infection with HCV-related virus or any mutated strain thereof, comprising administering to said human at least one peptide according to claim 6.

25. A method of immunizing a human against infection with HCV-related virus or any mutated strain thereof, comprising administering to said human at least one peptide according to claim 7.

26. A method of immunizing a human against infection with HCV-related virus or any mutated strain thereof, comprising administering to said human a combination of peptides according to any one of claims 1, 2 and 3.

27. A method for diagnosing exposure to or infection by HCV-related viruses comprising:

contacting anti-HCV-related virus antibodies within a sample of body fluid with at least one peptide according to any one of claims 1, 2 and 3, determining the binding of anti-HCV-related virus antibodies within a sample of body fluid with said at least one peptide.

28. The method according to claim 27 wherein said anti-HCV-related virus antibodies are anti-HCV antibodies.

29. A bioassay for identifying a compounds which modulate the interaction between a peptide according to any one of claims 1, 2 and 3 and an anti-HCV-related virus antibody, said bioassay comprising (i) determining the binding between said peptide and said anti-HCV-related virus antibody;

(ii) contacting said peptide with said compound;

(iii) adding said anti-HCV-related virus antibody to the peptide-compound complex formed in (ii);

(iv) after (iii), determining the binding between said peptide and said compound;

inferring, from (i) and (iv) the modulation of binding between said peptide and said anti-HCV-related virus antibody by said compound.

* * * * *

SEQUENCE LISTING

<160> NUMBER OF SEQ ID NOS: 41

<210> SEQ ID NO 1
<211> LENGTH: 35
<212> TYPE: PRT
<213> ORGANISM: Hepatitis C virus

<400> SEQUENCE: 1

Tyr Gln Val Arg Asn Ser Thr Gly Leu Tyr His Val Thr Asn Asp Cys
 1               5                  10                  15

Pro Asn Ser Ser Ile Val Tyr Glu Ala Ala Asp Ala Ile Leu His Thr
            20                  25                  30

Pro Gly Cys
        35

<210> SEQ ID NO 2
<211> LENGTH: 35
<212> TYPE: PRT
<213> ORGANISM: Hepatitis C virus

<400> SEQUENCE: 2

Tyr Glu Val Arg Asn Val Ser Gly Ile Tyr His Val Thr Asn Asp Cys
 1               5                  10                  15

Ser Asn Ser Ser Ile Val Tyr Glu Ala Ala Asp Met Ile Met His Thr
            20                  25                  30

Pro Gly Cys
        35

<210> SEQ ID NO 3
<211> LENGTH: 35
<212> TYPE: PRT
<213> ORGANISM: Hepatitis C virus

<400> SEQUENCE: 3

Val Glu Val Lys Asn Asn Ser Asn Ser Tyr Met Ala Thr Asn Asp Cys
 1               5                  10                  15

-continued

Ser Asn Ser Ser Ile Ile Trp Gln Leu Glu Gly Ala Val Leu His Thr
            20                  25                  30

Pro Gly Cys
        35

<210> SEQ ID NO 4
<211> LENGTH: 35
<212> TYPE: PRT
<213> ORGANISM: Hepatitis C virus

<400> SEQUENCE: 4

Val Glu Val Lys Asn Thr Ser Thr Ser Tyr Met Val Thr Asn Asp Cys
  1               5                  10                  15

Ser Asn Ser Ser Ile Val Trp Gln Leu Glu Gly Ala Val Leu His Thr
            20                  25                  30

Pro Gly Cys
        35

<210> SEQ ID NO 5
<211> LENGTH: 35
<212> TYPE: PRT
<213> ORGANISM: Hepatitis C virus

<400> SEQUENCE: 5

Leu Glu Trp Arg Asn Thr Ser Gly Leu Tyr Val Leu Thr Asn Asp Cys
  1               5                  10                  15

Ser Asn Ser Ser Ile Val Tyr Glu Ala Asp Asp Val Ile Leu His Thr
            20                  25                  30

Pro Gly Cys
        35

<210> SEQ ID NO 6
<211> LENGTH: 24
<212> TYPE: PRT
<213> ORGANISM: Hepatitis C virus

<400> SEQUENCE: 6

Leu Thr Asn Asp Cys Ser Asn Ser Ser Ile Val Tyr Glu Ala Asp Asp
  1               5                  10                  15

Val Ile Leu His Thr Pro Gly Cys
            20

<210> SEQ ID NO 7
<211> LENGTH: 35
<212> TYPE: PRT
<213> ORGANISM: Hepatitis C virus

<400> SEQUENCE: 7

Ile Asn Tyr Arg Asn Val Ser Gly Ile Tyr His Val Thr Asn Asp Cys
  1               5                  10                  15

Pro Asn Ser Ser Ile Val Tyr Glu Ala Asp His His Ile Leu His Leu
            20                  25                  30

Pro Gly Cys
        35

<210> SEQ ID NO 8
<211> LENGTH: 35
<212> TYPE: PRT
<213> ORGANISM: Hepatitis C virus

<400> SEQUENCE: 8

-continued

```
Val Pro Tyr Arg Asn Ala Ser Gly Ile Tyr His Ile Thr Asn Asp Cys
 1               5                  10                  15

Pro Asn Ser Ser Ile Val Tyr Glu Ala Asp Asn Leu Ile Leu His Ala
                20                  25                  30

Pro Gly Cys
        35

<210> SEQ ID NO 9
<211> LENGTH: 35
<212> TYPE: PRT
<213> ORGANISM: Hepatitis C virus

<400> SEQUENCE: 9

Leu Thr Tyr Gly Asn Ser Ser Gly Leu Tyr His Leu Thr Asn Asp Cys
 1               5                  10                  15

Ser Asn Ser Ser Ile Val Leu Glu Ala Asp Ala Met Ile Leu His Leu
                20                  25                  30

Pro Gly Cys
        35

<210> SEQ ID NO 10
<211> LENGTH: 29
<212> TYPE: PRT
<213> ORGANISM: Hepatitis C virus

<400> SEQUENCE: 10

Ile Val Tyr Glu Ala Ala Asp Met Ile Met His Thr Pro Gly Cys Val
 1               5                  10                  15

Pro Cys Val Arg Glu Asn Asn Ser Ser Arg Cys Trp Val
                20                  25

<210> SEQ ID NO 11
<211> LENGTH: 34
<212> TYPE: PRT
<213> ORGANISM: Hepatitis C virus

<400> SEQUENCE: 11

Val Arg Glu Asn Asn Ser Ser Arg Cys Trp Val Ala Leu Thr Pro Thr
 1               5                  10                  15

Leu Ala Ala Arg Asn Ala Ser Val Pro Thr Thr Thr Ile Arg Arg His
                20                  25                  30

Val Asp

<210> SEQ ID NO 12
<211> LENGTH: 36
<212> TYPE: PRT
<213> ORGANISM: Hepatitis C virus

<400> SEQUENCE: 12

Pro Cys Val Arg Glu Asn Asn Ser Ser Arg Cys Trp Val Ala Leu Thr
 1               5                  10                  15

Pro Thr Leu Ala Ala Arg Asn Ala Ser Val Pro Thr Thr Thr Ile Arg
                20                  25                  30

Arg His Val Asp
        35

<210> SEQ ID NO 13
<211> LENGTH: 30
<212> TYPE: PRT
<213> ORGANISM: Hepatitis C virus
```

```
<400> SEQUENCE: 13

His Val Asp Leu Leu Val Gly Ala Ala Ala Phe Cys Ser Ala Met Tyr
  1               5                  10                  15

Val Gly Asp Leu Cys Gly Ser Val Phe Leu Val Ser Gln Leu
             20                  25                  30

<210> SEQ ID NO 14
<211> LENGTH: 40
<212> TYPE: PRT
<213> ORGANISM: Hepatitis C virus

<400> SEQUENCE: 14

Ser Gln Leu Phe Thr Ile Ser Pro Arg Arg His Glu Thr Val Gln Asp
  1               5                  10                  15

Cys Asn Cys Ser Ile Tyr Pro Gly His Ile Thr Gly His Arg Met Ala
             20                  25                  30

Trp Asp Met Met Met Asn Trp Ser
         35                  40

<210> SEQ ID NO 15
<211> LENGTH: 34
<212> TYPE: PRT
<213> ORGANISM: Hepatitis C virus

<400> SEQUENCE: 15

Ser Ile Tyr Pro Gly His Ile Thr Gly His Arg Met Ala Trp Asp Met
  1               5                  10                  15

Met Met Asn Trp Ser Pro Thr Thr Ala Leu Val Val Ser Gln Leu Leu
             20                  25                  30

Arg Ile

<210> SEQ ID NO 16
<211> LENGTH: 41
<212> TYPE: PRT
<213> ORGANISM: Hepatitis C virus

<400> SEQUENCE: 16

Pro Gln Ala Val Val Asp Met Val Ala Gly Ala His Trp Gly Val Leu
  1               5                  10                  15

Ala Gly Leu Ala Tyr Tyr Ser Met Val Gly Asn Trp Ala Lys Val Leu
             20                  25                  30

Val Val Met Leu Leu Phe Ala Gly Val
         35                  40

<210> SEQ ID NO 17
<211> LENGTH: 32
<212> TYPE: PRT
<213> ORGANISM: Hepatitis C virus

<400> SEQUENCE: 17

His Thr Arg Val Ser Gly Gly Ala Ala Ala Ser Asn Thr Arg Gly Leu
  1               5                  10                  15

Val Ser Leu Phe Ser Pro Gly Ser Ala Gln Lys Ile Gln Leu Val Asn
             20                  25                  30

<210> SEQ ID NO 18
<211> LENGTH: 35
<212> TYPE: PRT
<213> ORGANISM: Hepatitis C virus
```

```
<400> SEQUENCE: 18

Leu Val Asn Thr Asn Gly Ser Trp His Ile Asn Arg Thr Ala Leu Asn
 1               5                  10                  15

Cys Asn Asp Ser Leu Gln Thr Gly Phe Phe Ala Ala Leu Phe Tyr Lys
                20                  25                  30

His Lys Phe
         35

<210> SEQ ID NO 19
<211> LENGTH: 38
<212> TYPE: PRT
<213> ORGANISM: Hepatitis C virus

<400> SEQUENCE: 19

Asn Asp Ser Leu Gln Thr Gly Phe Phe Ala Ala Leu Phe Tyr Lys His
 1               5                  10                  15

Lys Phe Asn Ser Ser Gly Cys Pro Glu Arg Leu Ala Ser Cys Arg Ser
                20                  25                  30

Ile Asp Lys Phe Ala Gln
         35

<210> SEQ ID NO 20
<211> LENGTH: 28
<212> TYPE: PRT
<213> ORGANISM: Hepatitis C virus

<400> SEQUENCE: 20

Arg Ser Ile Asp Lys Phe Ala Gln Gly Trp Gly Pro Leu Thr Tyr Thr
 1               5                  10                  15

Glu Pro Asn Ser Ser Asp Gln Arg Pro Tyr Cys Trp
                20                  25

<210> SEQ ID NO 21
<211> LENGTH: 34
<212> TYPE: PRT
<213> ORGANISM: Hepatitis C virus

<400> SEQUENCE: 21

Ser Asp Gln Arg Pro Tyr Cys Trp His Tyr Ala Pro Arg Pro Cys Gly
 1               5                  10                  15

Ile Val Pro Ala Ser Gln Val Cys Gly Pro Val Tyr Cys Phe Thr Pro
                20                  25                  30

Ser Pro

<210> SEQ ID NO 22
<211> LENGTH: 31
<212> TYPE: PRT
<213> ORGANISM: Hepatitis C virus

<400> SEQUENCE: 22

Ser Gln Val Cys Gly Pro Val Tyr Cys Phe Thr Pro Ser Pro Val Val
 1               5                  10                  15

Val Gly Thr Thr Asp Arg Phe Gly Val Pro Thr Tyr Asn Trp Gly
                20                  25                  30

<210> SEQ ID NO 23
<211> LENGTH: 44
<212> TYPE: PRT
<213> ORGANISM: Hepatitis C virus

<400> SEQUENCE: 23
```

```
Gly Val Pro Thr Tyr Asn Trp Gly Ala Asn Asp Ser Asp Val Leu Ile
 1               5                  10                  15

Leu Asn Asn Thr Arg Pro Pro Arg Gly Asn Trp Phe Gly Cys Thr Trp
             20                  25                  30

Met Asn Gly Thr Gly Phe Thr Lys Thr Cys Gly Gly
         35                  40
```

<210> SEQ ID NO 24
<211> LENGTH: 36
<212> TYPE: PRT
<213> ORGANISM: Hepatitis C virus

<400> SEQUENCE: 24

```
Ala Asn Asp Ser Asp Val Leu Ile Leu Asn Asn Thr Arg Pro Pro Arg
 1               5                  10                  15

Gly Asn Trp Phe Gly Cys Thr Trp Met Asn Gly Thr Gly Phe Thr Lys
             20                  25                  30

Thr Cys Gly Gly
         35
```

<210> SEQ ID NO 25
<211> LENGTH: 25
<212> TYPE: PRT
<213> ORGANISM: Hepatitis C virus

<400> SEQUENCE: 25

```
Thr Arg Pro Pro Arg Gly Asn Trp Phe Gly Cys Thr Trp Met Asn Gly
 1               5                  10                  15

Thr Gly Phe Thr Lys Thr Cys Gly Gly
             20                  25
```

<210> SEQ ID NO 26
<211> LENGTH: 30
<212> TYPE: PRT
<213> ORGANISM: Hepatitis C virus

<400> SEQUENCE: 26

```
Thr Lys Thr Cys Gly Gly Pro Pro Cys Asn Ile Gly Gly Ala Gly Asn
 1               5                  10                  15

Asn Thr Leu Thr Cys Pro Thr Asp Cys Phe Arg Lys His Pro
             20                  25                  30
```

<210> SEQ ID NO 27
<211> LENGTH: 45
<212> TYPE: PRT
<213> ORGANISM: Hepatitis C virus

<400> SEQUENCE: 27

```
Thr Asp Cys Phe Arg Lys His Pro Glu Ala Thr Tyr Ala Arg Cys Gly
 1               5                  10                  15

Ser Gly Pro Trp Leu Thr Pro Arg Cys Met Val His Tyr Pro Tyr Arg
             20                  25                  30

Leu Trp His Tyr Pro Cys Thr Val Asn Phe Thr Ile Phe
         35                  40                  45
```

<210> SEQ ID NO 28
<211> LENGTH: 33
<212> TYPE: PRT
<213> ORGANISM: Hepatitis C virus

<400> SEQUENCE: 28

-continued

```
Ala Arg Cys Gly Ser Gly Pro Trp Leu Thr Pro Arg Cys Met Val His
 1               5                  10                  15

Tyr Pro Tyr Arg Leu Trp His Tyr Pro Cys Thr Val Asn Phe Thr Ile
             20                  25                  30

Phe

<210> SEQ ID NO 29
<211> LENGTH: 25
<212> TYPE: PRT
<213> ORGANISM: Hepatitis C virus

<400> SEQUENCE: 29

Leu Thr Pro Arg Cys Met Val His Tyr Pro Tyr Arg Leu Trp His Tyr
 1               5                  10                  15

Pro Cys Thr Val Asn Phe Thr Ile Phe
             20                  25

<210> SEQ ID NO 30
<211> LENGTH: 28
<212> TYPE: PRT
<213> ORGANISM: Hepatitis C virus

<400> SEQUENCE: 30

Thr Val Asn Phe Thr Ile Phe Lys Val Arg Met Tyr Val Gly Gly Val
 1               5                  10                  15

Glu His Arg Phe Glu Ala Ala Cys Asn Trp Thr Arg
             20                  25

<210> SEQ ID NO 31
<211> LENGTH: 33
<212> TYPE: PRT
<213> ORGANISM: Hepatitis C virus

<400> SEQUENCE: 31

Glu Ala Ala Cys Asn Trp Thr Arg Gly Glu Arg Cys Asp Leu Glu Asp
 1               5                  10                  15

Arg Asp Arg Ser Glu Leu Ser Pro Leu Leu Ser Thr Thr Glu Trp
             20                  25                  30

Gln

<210> SEQ ID NO 32
<211> LENGTH: 36
<212> TYPE: PRT
<213> ORGANISM: Hepatitis C virus

<400> SEQUENCE: 32

Gln Trp Gln Ile Leu Pro Cys Ser Phe Thr Thr Leu Pro Ala Leu Ser
 1               5                  10                  15

Thr Gly Leu Ile His Leu His Gln Asn Ile Val Asp Val Gln Tyr Leu
             20                  25                  30

Tyr Gly Val Gly
        35

<210> SEQ ID NO 33
<211> LENGTH: 42
<212> TYPE: PRT
<213> ORGANISM: Hepatitis C virus

<400> SEQUENCE: 33

Gly Val Gly Ser Ala Val Val Ser Leu Val Ile Lys Trp Glu Tyr Val
```

```
                    1               5                  10                 15
Leu Leu Leu Phe Leu Leu Leu Ala Asp Ala Arg Ile Cys Ala Cys Leu
                   20                 25                 30
Trp Met Met Leu Leu Ile Ala Gln Ala Glu
            35                 40

<210> SEQ ID NO 34
<211> LENGTH: 34
<212> TYPE: PRT
<213> ORGANISM: Hepatitis C virus

<400> SEQUENCE: 34

Asn Thr Arg Gly Leu Val Ser Leu Phe Ser Pro Gly Ser Ala Gln Lys
 1               5                  10                 15
Ile Gln Leu Val Asn Thr Asn Gly Ser Trp His Ile Asn Arg Thr Ala
                20                  25                 30
Leu Asn

<210> SEQ ID NO 35
<211> LENGTH: 31
<212> TYPE: PRT
<213> ORGANISM: Hepatitis C virus

<400> SEQUENCE: 35

Asp Arg Ser Glu Leu Ser Pro Leu Leu Leu Ser Thr Thr Glu Trp Gln
 1               5                  10                 15
Ile Leu Pro Cys Ser Phe Thr Thr Leu Pro Ala Leu Ser Thr Gly
                20                  25                 30

<210> SEQ ID NO 36
<211> LENGTH: 20
<212> TYPE: PRT
<213> ORGANISM: Hepatitis C virus

<400> SEQUENCE: 36

Val Gly Thr Thr Asp Arg Phe Gly Val Pro Thr Tyr Asn Trp Gly Ala
 1               5                  10                 15
Asn Asp Ser Asp
            20

<210> SEQ ID NO 37
<211> LENGTH: 40
<212> TYPE: PRT
<213> ORGANISM: Hepatitis C virus

<400> SEQUENCE: 37

Val Ala Leu Thr Pro Thr Leu Ala Ala Arg Asn Ala Ser Val Pro Thr
 1               5                  10                 15
Thr Thr Ile Arg Arg His Val Asp Ser Gln Leu Phe Thr Ile Ser Pro
                20                  25                 30
Arg Arg His Glu Thr Val Gln Asp
            35                 40

<210> SEQ ID NO 38
<211> LENGTH: 36
<212> TYPE: PRT
<213> ORGANISM: Hepatitis C virus

<400> SEQUENCE: 38

Thr His Ala Cys Arg Ala Asn Gly Gln Tyr Phe Leu Thr Asn Cys Cys
 1               5                  10                 15
```

-continued

```
Ala Pro Glu Asp Ile Gly Phe Cys Leu Glu Gly Gly Cys Leu Val Ala
                20                  25                  30

Leu Gly Gly Lys
        35

<210> SEQ ID NO 39
<211> LENGTH: 16
<212> TYPE: PRT
<213> ORGANISM: Hepatitis C virus

<400> SEQUENCE: 39

Ser Gln Leu Phe Thr Ile Ser Pro Arg Arg His Glu Thr Val Gln Asp
1               5                   10                  15

<210> SEQ ID NO 40
<211> LENGTH: 35
<212> TYPE: PRT
<213> ORGANISM: Hepatitis C virus

<400> SEQUENCE: 40

Leu Ile Asn Thr Asn Gly Ser Trp His Ile Asn Arg Thr Ala Leu Asn
1               5                   10                  15

Cys Asn Asp Ser Leu His Thr Gly Phe Leu Ala Ser Leu Phe Tyr Thr
                20                  25                  30

His Ser Phe
        35

<210> SEQ ID NO 41
<211> LENGTH: 30
<212> TYPE: PRT
<213> ORGANISM: Hepatitis C virus

<400> SEQUENCE: 41

Arg Ser Ile Glu Ala Phe Arg Val Gly Trp Gly Ala Leu Gln Tyr Glu
1               5                   10                  15

Asp Asn Val Thr Asn Pro Glu Asp Met Arg Pro Tyr Cys Trp
                20                  25                  30
```